(12) United States Patent
Gjerde et al.

(10) Patent No.: US 8,501,116 B2
(45) Date of Patent: *Aug. 6, 2013

(54) LOW DEAD VOLUME EXTRACTION COLUMN DEVICE

(75) Inventors: Douglas T. Gjerde, Saratoga, CA (US); Christopher P. Hanna, Elmhurst, IL (US)

(73) Assignee: PhyNexus, Inc., San Jose, CA (US)

( * ) Notice: Subject to any disclaimer, the term of this patent is extended or adjusted under 35 U.S.C. 154(b) by 44 days.

This patent is subject to a terminal disclaimer.

(21) Appl. No.: 13/206,435

(22) Filed: Aug. 9, 2011

(65) Prior Publication Data

US 2011/0293490 A1     Dec. 1, 2011

Related U.S. Application Data

(63) Continuation of application No. 12/329,319, filed on Dec. 5, 2008, now abandoned, which is a continuation of application No. 10/620,155, filed on Jul. 14, 2003, now Pat. No. 7,482,169.

(51) Int. Cl.
*B01L 3/00*     (2006.01)

(52) U.S. Cl.
USPC .......................................................... 422/501

(58) Field of Classification Search
USPC .......................................................... 422/501
See application file for complete search history.

(56) References Cited

U.S. PATENT DOCUMENTS 7,482,169 B2 *  1/2009  Gjerde et al. ............... 436/178
7,488,603 B2 *  2/2009  Gjerde et al. ............... 436/177

* cited by examiner

*Primary Examiner* — Lore Jarrett
(74) *Attorney, Agent, or Firm* — Sue S. Kalman

(57) ABSTRACT

The invention provides extraction columns for the purification of an analyte (e.g., a biological macromolecule, such as a peptide, protein or nucleic acid) from a sample solution, as well as methods for making and using such columns. The invention is characterized by the use of low dead volume columns, which is achieved in part by the use of low pore volume frits (e.g., membrane screens) to contain a bed of extraction media in the column. Low dead volume facilitates the elution of the captured analyte into a very small volume of desorption solution, allowing for the preparation of low volume samples containing relatively high concentrations of analyte.

18 Claims, 7 Drawing Sheets

LOW DEAD VOLUME EXTRACTION COLUMN DEVICE

CROSS-REFERENCE TO RELATED APPLICATIONS

This patent application is a continuation of U.S. patent application Ser. No. 12/329,319, filed Dec. 5, 2008 now abandoned, which is a continuation of U.S. patent application Ser. No. 10/620,155 filed Jul. 14, 2003, now U.S. Pat. No. 7,482,169, both of which are incorporated by reference herein in their entirety for all purposes.

FIELD OF THE INVENTION

This invention relates to a device and method for the capture of analytes by solid phase extraction with a column device and collection of the analytes into a controlled volume of solvent. The analytes can include biomolecules, particularly biological macromolecules such as proteins and peptides. The device and method of this invention are particularly useful in proteomics for sample preparation and analysis with analytical technologies employing biochips, mass spectrometry and other instrumentation.

BACKGROUND OF THE INVENTION

Proteomics can be defined as the comprehensive study of proteins and their functional aspects. Proteins perform the work of the cell. Single proteins can have many forms. The function of a protein depends on the form, interactions, and complexes of the protein. A deeper understanding of the biological functions of proteins is needed so that drugs can be developed.

Protein sample processing is a complex problem within proteomics. Proteins can function individually or as complexes (groups of proteins bound as a complex). Proteins cannot be amplified, as DNA is amplified with polymerase chain reaction (PCR) methods. Proteins must be enriched and purified before they can be analyzed. Protein processing methods and systems must be flexible; more than a million possible proteins are expressed. For analysis it is necessary to separate and concentrate the proteins of interest from many thousands of other proteins, while selectively removing other materials that will interfere with the protein analytical process including cellular material such as other proteins, sugars, carbohydrates, lipids, DNA, RNA and salts. Reproducible recovery is needed and in most cases protein function must be retained during processing. Structural differences between forms must be preserved and final processing of samples must be easily integrated into many different detection schemes, for example mass spectrometry, protein chips, and the like.

Solid phase extraction is one of the primary tools for preparing protein samples prior to analysis. The method purifies proteins according to their identity, class type or structure, or function to prepare them for analysis by mass spectrometry or other analytical methods.

The process of solid phase extraction uses an extraction phase in the form of a column or bed, and the sample may be either loaded onto the column or added to a bulk solution to extraction beads. The extraction phase retains the sample protein, the extraction phase is washed to remove contaminants, and then the sample protein is removed with the extraction or recovery solvent.

Extraction columns are used to prepare the protein samples for analysis. Often very low amounts of proteins are expressed in a sample, and sample preparation procedures are needed to isolate and recover the protein before analysis.

The solid phase extraction of biomolecules such as nucleic acids and proteins is commonly performed by columns packed with a variety of extraction phases.

The need for biomolecule extraction for proteins is increasing rapidly. Large numbers of samples need to be analyzed by a variety of techniques to determine the function of proteins. Typical sample volume is 0.5 to 5 mL or more on a typical column bed volume of 1 to 5 mL, requiring a typical desorption solvent volume of 2 to 10 mL.

There are a number of companies that have developed products whose principle aim is the purification of certain proteins or protein classes by solid phase extraction. The intent of these products is the simplification of proteomic analyses by providing a sample of only those proteins in which the investigator is interested. These products are often packaged for a single use and disposal. Packed-bed columns operate at relatively low pressures, thus making them simple to operate in a highly parallel and automated manner. Due to the very nature of a conventional packed-bed approach, it is limited with respect to reliable quantification and/or enrichment of sample. A packed-bed approach is extremely difficult to apply in a manner that is both cost-effective and reliable. It cannot be effectively applied to a microscale process level.

Moreover, packed columns have extensive carry-over from sample to sample, are expensive to manufacture, and may be difficult to multiplex (extract multiple samples simultaneously). Proteins may be irreversibly adsorbed to the extraction phase or may be trapped by frits and other "dead zones" within the column making recovery of the proteins incomplete.

Other drawbacks include losses of materials due to unswept volumes leading to low recoveries and irreproducibility of results; dilution of materials due to large elution volumes applied in an attempt to minimize these selfsame unswept volumes; depending on implementation, requirements often to adhere to a flow "directionality" introducing limitations on full integration of sample processing; manufacturing difficulties and costs for micro- or nanoscale volume systems; and porosity of construction materials used in commercially available systems that cause severe loss of biomaterials.

Spin columns and pipette tip columns are disposable column technologies commonly used for processing samples. At present, most of these columns contain filters or frits. Conventional frits, porous discs used to contain the column beds, have significant dead volume. This leads to significant sample loss when very small sample volumes are separated.

One conventional method for making sample preparation devices involves first inserting a precut porous plug obtained from, for example, a fibrous glass or cellulose sheet, into the tip of a pipette. This is followed by the addition of loose particles and a second porous plug. The plugs serve to retain the particles in place in the pipette tip. However, the plugs also entrap excess liquid thereby creating dead space or volume (i.e., space not occupied by media or polymer that can lead to poor sample recovery, contamination such as by sample carry-over, etc.).

Current available methods are not well suited for the separation and recovery of very small volumes in the low microliter range.

Also, since the volume of the filter is often as large as the volume of the micro volume sample itself, the extraction or separation process or chromatography process is adversely affected due to the large volume of filter material through which the sample must pass.

In addition, the adsorption of biomolecules can be a problem. Since the concentration of biomolecules in micro volume samples is so small, the adsorption of biomolecules on the filter can result in significant loss of the total sample mass. The filter material may also absorb proteins or biomolecules from the sample, resulting in lower than desirable sample recovery. Also, the filter material may behave differently in different elution media, subsequently interfering with both the quality of the separation process and the volume of the sample retained.

Collecting samples in the 1 to 20 µL range is a critical need. At such low volumes, efficient sample handling is crucial to avoid loss. Conventional methods and devices for sample preparation are not practical for handling the "microseparation" of such small sample volumes.

Ultrafiltration can only effectively concentrate and desalt, and thus the application of adsorption technology at this scale could offer an entirely new approach to micro-mass sample preparation.

However, these procedures cannot be used with extremely small liquid delivery devices such as conventional pipette tips, as there is no practical way to load either the plug or the particles to obtain a micro-adsorptive device that contains 20 milligrams or less of adsorbent, the amount suitable for use with the aforementioned extremely small sample loads.

DESCRIPTION OF SPECIFIC EMBODIMENTS OF THE INVENTION

Figure 1:
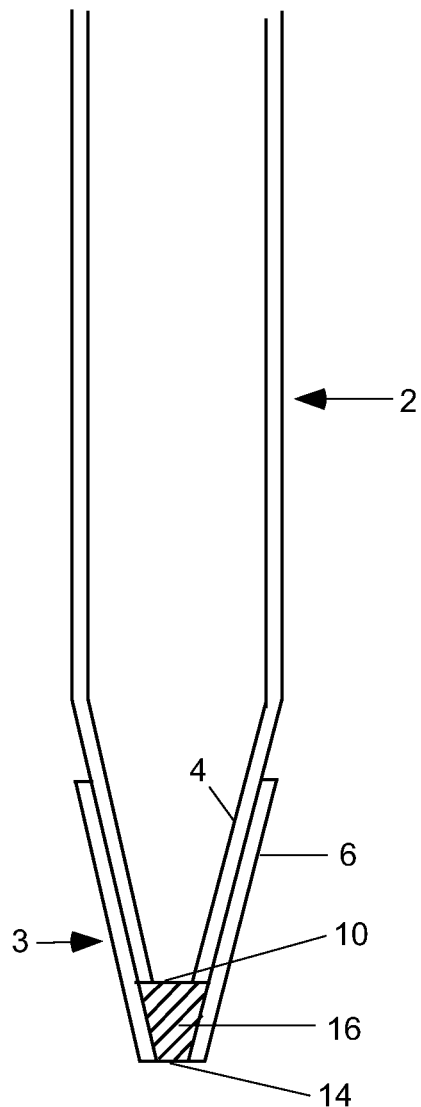
FIG. 1 depicts an embodiment of the invention where the extraction column body is constructed from a tapered pipette tip.

This invention is used for the capture of analytes by solid phase extraction with a column device and collection of the analytes into a controlled volume of solvent. This invention is useful for analytes including biomolecules and is compatible with requirements for sample preparation and analysis by analytical technology—especially biochips and mass spectrometry.

The invention is characterized by the use of extraction columns having low dead volumes. This is achieved in part by the use of a low volume frit or frits to contain a bed of extraction media in an extraction media chamber positioned in the column. Low dead volume facilitates the elution of the captured analyte into a very small volume of desorption solution, allowing for the preparation of low volume samples containing relatively high concentrations of analyte. Low volume, high concentration solutions particularly useful with regard to protein preparations for analysis by techniques such as mass spectrometery and protein chips.

I. Terminology

Before describing the present invention in detail, it is to be understood that this invention is not limited to specific embodiments described herein. It is also to be understood that the terminology used herein for the purpose of describing particular embodiments is not intended to be limiting. As used in this specification and the appended claims, the singular forms "a", "an" and "the" include plural referents unless the context clearly dictates otherwise. Thus, for example, reference to polymer bearing a protected carbonyl would include a polymer bearing two or more protected carbonyls, and the like.

Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, specific examples of appropriate materials and methods are described herein.

In describing and claiming the present invention, the following terminology will be used in accordance with the definitions set out below.

The term "bed volume" as used herein is defined as the volume of a bed of extraction media in an extraction column. Depending on how densely the bed is packed, the volume of the extraction media in the column bed is typically about half to one third of the total bed volume; well packed beds have less space between the beads and hence generally have lower interstital volumes.

The term "interstitial volume" of the bed refers to the volume of the bed of extraction media that is accessible to solvent, e.g., aqueous sample solutions, wash solutions and desorption solvents. For example, in the case where the extraction media is a chromatography bead (e.g., agarose or sepharose), the interstitial volume of the bed constitutes the solvent accessible volume between the beads, as well as any solvent accessible internal regions of the bead, e.g., solvent accessible pores. The interstitial volume of the bed represents the minimum volume of liquid required to saturate the column bed.

The term "dead volume" as used herein with respect to a column is defined as the interstitial volume of the extraction bed, tubes, membrane or frits, and passageways in a column. In the device of this invention with gel-type extraction media and the pore volume of the frits. Since the bottom frit of the column directly contacts the sample, wash, and elution liquids, minimal tubing or passageway dead volume is present in this device.

The term "elution volume" as used herein is defined as the volume of desorption or elution liquid into which the analytes are desorbed and collected. The terms "desorption solvent," elution liquid" and the like are used interchangeably herein.

The term "enrichment factor" as used herein is defined as the ratio of the sample volume divided by the elution volume, assuming that there is no contribution of liquid coming from the dead volume. To the extent that the dead volume either dilutes the analytes or prevents complete adsorption, the enrichment factor is reduced.

The terms "extraction column" and "extraction tip" as used herein are defined as a column device used in combination with a pump, the column device containing a bed of solid phase extraction material, i.e., extraction media.

The term "frit" as used herein are defined as porous material for holding the extraction media in place in a column. An extraction media chamber is typically defined by a top and bottom frit positioned in an extraction column. In preferred embodiments of the invention the frit is thin, and has a low pore volume, e.g., a membrane screen.

The term "gel-type packing material" as used herein is defined as non-porous or micro-porous beads such as agarose or sepharose beads, the beads containing a functional group or having a surface that binds selectively with the analyte of interest.

The term "lower column body" as used herein is defined as the column bed and bottom membrane screen of a column.

The term "membrane screen" as used herein is defined as a woven or non-woven fabric or screen for holding the column packing in place in the column bed, the membranes having a low dead volume. The membranes are of sufficient strength to withstand packing and use of the column bed and of sufficient porosity to allow passage of liquids through the column bed. The membrane is thin enough so that it can be sealed around the perimeter or circumference of the membrane screen so that the liquids flow through the screen.

The term "sample volume", as used herein is defined as the volume of the liquid of the original sample solution from which the analytes are separated or purified.

The term "upper column body", as used herein is defined as the chamber and top membrane screen of a column.

The term "biomolecule" as used herein refers to biomolecule derived from a biological system. The term includes biological macromolecules, such as a proteins, peptides, and nucleic acids.

The term "protein chip" is defined as a small plate or surface upon which an array of separated, discrete protein samples are to be deposited or have been deposited. These protein samples are typically small and are sometimes referred to as "dots." In general, a chip bearing an array of discrete proteins is designed to be contacted with a sample having one or more biomolecules which may or may not have the capability of binding to the surface of one or more of the dots, and the occurrence or absence of such binding on each dot is subsequently determined. A reference that describes the general types and functions of protein chips is Gavin MacBeath, *Nature Genetics Supplement,* 32:526 (2002).

II. Low Dead Volume Extraction Columns

Column Body

The column body is a tube having two open ends connected by an open channel. The tube can be in any shape, including but not limited to cylindrical or frustoconical, and of any dimensions consistent with the function of the column as described herein. In certain embodiments of the invention the column body takes the form of a pipette tip, a syringe, a luer adapter or similar tubular bodies.

One of the open ends of the column, sometimes referred to herein as the open upper end of the column, is adapted for attachment to a pump. In some embodiments of the invention the upper open end is operatively attached to a pump, whereby the pump can be used for aspirating a fluid into the extraction column through the other open end of the column, and optionally for discharging fluid out through the open lower end of the column. Thus, it is a feature of the present invention that fluid enters and exits the extraction column through the same open end of the column. This is in contradistinction with the operation of some extraction columns, where fluid enters the column through one open end and exits through the other end after traveling through an extraction media, i.e., similar to conventional column chromatography. The fluid can be a liquid, such as a sample solution, wash solution or desorption solvent.

The column body can be can be composed of any material that is sufficiently non-porous that it can retain fluid and that is compatible with the solutions, media, pumps and analytes used. A material should be employed that does not substantially react with substances it will contact during use of the extraction column, e.g., the sample solutions, the analyte of interest, the extraction media and desorption solvent. A wide range of suitable materials are available and known to one of skill in the art, and the choice is one of design. Various plastics make ideal column body materials, but other materials such as glass, ceramics or metals could be used in some embodiments of the invention. Some examples of materials include polysulfone, polypropylene, polyethylene, polyethyleneterephthalate, polyethersulfone, polytetrafluoroethylene, cellulose acetate, cellulose acetate butyrate, acrylonitrile PVC copolymer, polystyrene, polystyrene/acrylonitrile copolymer, polyvinylidene fluoride, glass, metal, silica, and combinations of the above listed materials.

Some specific examples of suitable column bodies are provided in the Examples.

Extraction Media

The extraction media used in the column is preferably a form of water-insoluble particle (e.g., a porous or non-porous bead) that has an affinity for an analyte of interest. Typically the analyte of interest is a protein, peptide or nucleic acid. The extraction processes can be affinity, reverse phase, normal phase, ion exchange, hydrophobic interaction chromatography, or hydrophilic interaction chromatography agents.

The bed volume of the extraction media used in the extraction columns of the invention is typically small, preferably in the range of 0.5-100 µL, more preferably in the range of 1-50 µL, and still more preferably in the range of 2-25 µL. The low bed volume results in a low interstitial volume of the bed, contributing to the low dead volume of the column, thereby facilitating the recovery of the analyte in a small volume of desorption solvent.

The low bed volumes employed in certain embodiments allow for the use of relatively small amounts of extraction media, e.g., soft, gel-type beads. For example, some embodiments of the invention employ a bed of extraction media having a dry weight of less than 10 mg (e.g., in the range of 0.1-10 mg, 0.5-10 mg, 1-10 mg or 2-10 mg), less than 2 ms (e.g., in the range of 0.1-2 mg, 0.5-2 mg or 1-2 mg), or less than 1 mg (e.g., in the range of 0.1-1 mg or 0.5-1 mg).

Many of the extraction media types suitable for use in the invention are selected from a variety of classes of chromatography media. It has been found that many of these chromatography media types and the associated chemistries are suited for use as solid phase extraction media in the devices methods of this invention.

Thus, examples of suitable extraction media include agarose-based materials, sepharose-based materials, polystyrene/divinylbenzene copolymers, poly methylmethacrylate, protein G beads (e.g., for IgG protein purification), MEP Hypercel™ beads (e.g., for IgG protein purification), affinity phase beads (e.g., for protein purification), ion exchange phase beads (e.g., for protein purification), hydrophobic interaction beads (e.g., for protein purification), reverse phase beads (e.g., for nucleic acid or protein purification), and beads having an affinity for molecules analyzed by label-free detection. Silica beads are also suitable.

Soft gel-type beads, such as agarose and sepharose based beads, are found to work surprisingly well in columns and methods of this invention. In conventional chromatography fast flow rates can result in bead compression, which results in increased back pressure and adversely impacts the ability to use these gels with faster flow rates. In the present invention relatively small bed volumes are used, and it appears that this allows for the use of high flow rates with a minimal amount of bead compression and the problem attendant with such compression.

Affinity extractions use a technique in which a biospecific adsorbent is prepared by coupling a specific ligand (such as an enzyme, antigen, or hormone) for the analyte, (e.g., macromolecule) of interest to a solid support. This immobilized ligand will interact selectively with molecules that can bind to it. Molecules that will not bind elute unretained. The interaction is selective and reversible. The references listed below show examples of the types of affinity groups that can be employed in the practice of this invention are hereby incorporated by reference herein in their entireties. Antibody Purification Handbook, *Amersham Biosciences*, Edition AB, 18-1037-46 (2002); Protein Purification Handbook, *Amersham Biosciences*, Edition AC, 18-1132-29 (2001); Affinity Chromatography Principles and Methods, *Amersham Pharmacia Biotech*, Edition AC, 18-1022-29 (2001); The Recombinant Protein Handbook, *Amersham Pharmacia Biotech*, Edition AB, 18-1142-75 (2002); and *Protein Purification: Principles, High Resolution Methods, and Applications*, Jan-Christen Janson (Editor), Lars G. Ryden (Editor), Wiley, John & Sons, Incorporated (1989).

Examples of suitable affinity binding agents are summarized in Table I, wherein the affinity agents are from one or more of the following interaction categories:
1. Chelating metal—ligand interaction
2. Protein—Protein interaction
3. Organic molecule or moiety—Protein interaction
4. Sugar—Protein interaction
5. Nucleic acid—Protein interaction
6. Nucleic acid—nucleic acid interaction

TABLE I

| Examples of Affinity molecule or moiety fixed at surface | Captured biomolecule | Interaction Category |
|---|---|---|
| Ni-NTA | His-tagged protein | 1 |
| Ni-NTA | His-tagged protein within a multi-protein complex | 1, 2 |
| Fe-IDA | Phosphopeptides, phosphoproteins | 1 |
| Fe-IDA | Phosphopeptides or phosphoproteins within a multi-protein complex | 1, 2 |
| Antibody or other Proteins | Protein antigen | 2 |
| Antibody or other Proteins | Small molecule-tagged protein | 3 |
| Antibody or other Proteins | Small molecule-tagged protein within a multi-protein complex | 2, 3 |
| Antibody or other Proteins | Protein antigen within a multi-protein complex | 2 |
| Antibody or other Proteins | Epitope-tagged protein | 2 |
| Antibody or other Proteins | Epitope-tagged protein within a multi-protein complex | 2 |
| Protein A, Protein G or Protein L | Antibody | 2 |
| Protein A, Protein G or Protein L | Antibody | 2 |
| ATP or ATP analogs; 5'-AMP | Kinases, phosphatases (proteins that requires ATP for proper function) | 3 |
| ATP or ATP analogs; 5'-AMP | Kinase, phosphatases within multi-protein complexes | 2, 3 |
| Cibacron 3G | Albumin | 3 |
| Heparin | DNA-binding protein | 4 |
| Heparin | DNA-binding proteins within a multi-protein complex | 2, 4 |

TABLE I-continued

| Examples of Affinity molecule or moiety fixed at surface | Captured biomolecule | Interaction Category |
|---|---|---|
| Lectin | Glycopeptide or glycoprotein | 4 |
| Lectin | Glycopeptide or glycoprotein within a multi-protein complex | 2, 4 |
| ssDNA or dsDNA | DNA-binding protein | 5 |
| ssDNA or dsDNA | DNA-binding protein within a multi-protein complex | 2, 5 |
| ssDNA | Complementary ssDNA | 6 |
| ssDNA | Complementary RNA | 6 |
| Streptavidin/Avidin | Biotinylated peptides (ICAT) | 3 |
| Streptavidin/Avidin | Biotinylated engineered tag fused to a protein (see avidity.com) | 3 |
| Streptavidin/Avidin | Biotinylated protein | 3 |
| Streptavidin/Avidin | Biotinylated protein within a multi-protein complex | 2, 3 |
| Streptavidin/Avidin | Biotinylated engineered tag fused to a protein within a multi-protein complex | 2, 3 |
| Streptavidin/Avidin | Biotinylated nucleic acid | 3 |
| Streptavidin/Avidin | Biotinylated nucleic acid bound to a protein or multi-protein complex | 2, 3 |
| Streptavidin/Avidin | Biotinylated nucleic acid bound to a complementary nucleic acid | 3, 6 |

In one aspect of the invention an extraction media is used that contains a surface functionality that has an affinity for a protein fusion tag used for the purification of recombinant proteins. A wide variety of fusion tags and corresponding affinity groups are available and can be used in the practice of the invention.

One of the most common fusion tags is the so-called "His" tag, which is comprised of a series of consecutive histidine residues, e.g., two, four or six consecutive histidine residues. There are a number of metal-chelate groups that can be attached to the surface of an extraction media for purification of "His-tagged proteins, including metal-IDA (IDA: iminodiacetate), metal-NTA (NTA: nitrilotriacetate), and metal-CMA (CMA: carboxymethylated aspartate), where the metal is typically selected from nickel, copper, iron, zinc and cobalt. The trapped fusion protein is eluted by disrupting the histidine-metal coordination by some suitable salt such as imidazole or ethylene diamine tetra acetic acid (EDTA).

There are other affinity groups available for purifying recombinant proteins through their fusion tags, and these groups can be attached to an extraction media for use in the invention. Antibodies can be used for purification through any peptide sequence (a common one is the FLAG tag); avidin (monomeric or multimeric) can be used for purifying a peptide sequence that is selectively biotinylated within the expression system; calmodulin charged with calcium can be used for purifying a peptide sequence that is often referred to as a "calmodulin binding peptide" (or, CBP), where elution is performed by removing the calcium with ethylene glycol tetra acetic acid (EGTA); glutathione can be used for purifying a fusion protein that carries the glutathione S-transferase protein (GST), where the GST is often cleaved off with a specific protease; amylose can be used for purifying a fusion protein that carries the maltose binding protein (MBP), where the MBP is often cleaved off with a specific protease; cellulose can be used for purifying a fusion protein that carries a peptide that is referred to as the cellulose-binding domain tag, followed by elution with ethylene glycol; S-protein (derived from ribonuclease A) can be used for purifying a fusion protein that carries a peptide with specific affinity for S-protein, where the peptide can be cleaved off with a specific protease.

It is also possible to create an affinity surface that has the bis-arsenical fluorescein dye FlAsH. For example, a FlAsH dye can be used for purifying a fusion protein that carries the peptide sequence tag CCxxCC (where xx is any amino acid, such as RE). The protein is then eluted with 1,4-dithiothreitol, or DTT.

In one aspect the invention is used for purification of antibodies. Antibodies are frequently purified on the basis of highly conserved structural characteristics. For example, it is possible to pack columns with extraction media containing Protein A, Protein G, or Protein A/G fusions to purify IgG antibodies through their Fc region (with lower affinity for the Fab antibody fragment region in the case of Protein G). These are often eluted by using low pH 2.5. It is also possible to purify IgG antibodies through their Fab antibody fragment region, provided their light chain is a kappa light chain. This is achieved by using a surface of Protein L.

In one aspect the extraction media comprises small molecule ligands that are capable of achieving separations on the basis of hydrophobic charge interactions. Ligands such as 4-mercapto-ethyl-pyridine and 2-mercaptopyridine are capable of trapping antibodies such as IgGs, which are eluted by changes to low pH much milder than in the case of Protein A or Protein G. For example, elution is accomplished with 4-mercapto-ethyl-pyridine at pH 4 (as opposed to pH 2.5 for the Protein A and Protein G).

In addition, other antibodies can be used for purification of antibodies. For example, it is possible to use an extraction media comprising an immobilized antibody for the purification of IgE (with an anti-IgE surface), the purification of IgM (with an anti-IgM surface), the purification of IgA (with an anti-IgA surface), the purification of IgD (with an anti-IgD surface), as well as the purification of IgG (with an anti-IgG surface).

Extraction columns of the invention can be used for purification of phosphopeptides and phosphoproteins by the inclusion of an appropriate affinity group on the extraction media. One alternative is to exploit the natural interaction between phosphate groups and metal ions. Therefore, phosphopeptides and phosphoproteins can be purified on metal-chelate surfaces made from IDA, NTA, or CMA.

It is also possible to purify these phosphopeptides and phosphoproteins with immobilized antibodies. For example, it is possible to use antibodies on the packing material that are specific to phosphotyrosine residues, as well as phosphoserine and phosphothreonine residues. It is also possible to use antibodies that are bind to specific phosphorylated sites within a protein, such as specifically-binding phosphorylated tyrosine within a specific kinase. These antibodies are often referred to as phosphorylation site-specific antibodies (PS-SAs). Once adsorbed the trapped phosphoprotein and phosphopeptides can be eluted at low pH.

Yet another approach to the purification of phosphopeptides and phosphoproteins involves the derivatization of the phosphate group such that biotin is attached to it. This biotinylated phosphoprotein or phosphopeptide can be purified using an avidin-derivatized extraction media, wherein the avidin can be monomeric or multimeric.

In some embodiments of the invention an extraction column is used for the purification of protein complexes. One embodiment involves the use of a recombinant "bait" protein that will form complexes with its natural interaction partners. These multiprotein complexes are then purified through a fusion tag that is attached to the "bait." These tagged "bait" proteins can be purified through groups incorporated into the extraction media such as metal-chelate groups, antibodies, calmodulin, or any of the other surface groups described above for the purification of recombinant proteins.

It is also possible to purify "native" (i.e. non-recombinant) protein complexes without having to purify through a fusion tag. This is achieved by immobilizing an antibody for one of the proteins within the multiprotein complex. This process is often referred to as "co-immunoprecipitation." The multiprotein complexes can be eluted with low pH.

Extraction columns of the invention can be used to purify entire classes of proteins on the basis of highly conserved motifs within their structure, whereby an affinity ligand attached to the packing reversibly binds to the conserved motif. For example, it is possible to immobilize particular nucleotides on the extraction media. Examples include, but are not limited to, adenosine 5'-triphosphate (ATP), adenosine 5'-diphosphate (ADP), adenosine 5'-monophosphate (AMP), nicotinamide adenine dinucleotide (NAD), or nicotinamide adenine dinucleotide phosphate (NADP). These nucleotides can be used for the purification of enzymes that are dependent upon these nucleotides such as kinases, phosphatases, heat shock proteins and dehydrogenases, to name a few.

There are other affinity groups that can be incorporated into the extraction media for purification of protein classes. Lectins can be used for the purification of glycoproteins. Concanavilin A (Con A) and lentil lectin can be used for the purification of glycoproteins and membrane proteins, and wheat germ lectin can be used for the purification of glycoproteins and cells (especially T-cell lymphocytes). Though it is not a lectin, the small molecule phenylboronic acid can also be incorporated into the extraction media and used for purification of glycoproteins.

It is also possible to incorporate heparin into the extraction media, which is useful for the purification of DNA-binding proteins (e.g. RNA polymerase I, II and III, DNA polymerase, DNA ligase). In addition, immobilized heparin can be used for purification of various coagulation proteins (e.g. antithrombin III, Factor VII, Factor IX, Factor XI, Factor XII and XIIa, thrombin), other plasma proteins (e.g. properdin, BetaIH, Fibronectin, Lipses), lipoproteins (e.g. VLDL, LDL, VLDL apoprotein, HOLP, to name a few), and other proteins (platelet factor 4, hepatitis B surface antigen, hyaluronidase). These types of proteins are often blood and/or plasma borne. Since there are many efforts afoot to rapidly profile the levels of these types of proteins by technologies such as protein chips, the performance of these chips will be enhanced by performing an initial purification and enrichment of the targets prior to protein chip analysis.

It is also possible to use extraction media with protein interaction domains for purification of those proteins that are meant to interact with that domain. One interaction domain that can be used is the Src-homology 2 (SH2) domain that binds to specific phophotyrosine-containing peptide motifs within various proteins. The SH2 domain has previously been immobilized on a resin and used as an affinity reagent for performing affinity chromatography/mass spectrometry experiments for investigating in vitro phosphorylation of epidermal growth factor receptor (EGFR) (see Christian Lombardo, et al., Biochemistry, 34:16456 (1995)). Other than the SH2 domain, other protein interaction domains can be used for the purposes of purifying those proteins that possess their recognition domains. Many of these protein interaction domains have been described (see Tony Pawson, Protein Interaction Domains, *Cell Signaling Technology Catalog*, 264-279 (2002)) for additional examples of these protein interaction domains).

Benzamidine is another example of a class-specific affinity ligand, which can be incorporated into the extraction media for purification of serine proteases. The dye ligand Procion Red HE-3B can be used for the purification of dehydrogenases, reductases and interferon, to name a few.

Reversed-phase chromatography media can also function as an extraction media in certain embodiments of the invention. In reversed-phase chromatography, an aqueous/organic solvent mixture is commonly used as the mobile phase, and a high-surface-area nonpolar solid is employed as the stationary phase. The latter can be an alkyl-bonded silica packing, e.g., with $C_8$ or $C_{18}$ groups covering the silica surface. The basis of solute retention in reversed-phase chromatography is still somewhat controversial; some workers favor an adsorption, while others believe that the solute partitions into the nonpolar stationary phase. Probably both processes are important for many samples. Competition between solute and mobile-phase molecules exists for a place on the stationary-phase surface. That is, an adsorbed molecule will displace some number of previously adsorbed molecules (*Chromatography*, $5^{th}$ edition, PART A: FUNDAMENTALS AND TECHNIQUES, editor: E. Heftmann, Elsevier Science Publishing Company, New York, pp A25 (1992)). The near universal application of reversed-phase chromatography stems from the fact that virtually all organic molecules have hydrophobic regions in their structure and are capable of interacting with the stationary phase. Since the mobile phase is polar and generally contains water, the method is ideally suited to the separation of polar molecules which are either insoluble in organic solvents or bind too strongly to inorganic oxide adsorbents for normal elution. Reversed-phase chromatography employing acidic, low ionic strength eluents has become a widely established technique for the purification and structural elucidation of proteins. However, the structure of biopolymers is very sensitive to mobile phase composition, pH and the presence of complexing species which can result in anomalous retention and even denaturing of proteins. A general characteristic of reversed-phase systems is that a decrease in polarity of the mobile phase, that is increasing the volume fraction of organic solvent in an aqueous organic mobile phase, leads to a decrease in retention; a reversal of the general trends observed in liquid-solid chromatography or normal phase chromatography. It is also generally observed for reversed-phase chromatography that for members of a homologous or oligomous series, the logarithm of the solute capacity factor is a linear function of the number of methylene groups or repeat units of the oligomeric structure (ADVANCED CHROMATOGRAPHIC AND ELECTROMIGRATION METHODS IN BIOSCIENCES, editor: Z. Deyl, Elsevier Science BV, Amsterdam, The Netherlands, pp 528 (1998); CHROMATOGRAPHY TODAY, Colin F. Poole and Salwa K. Poole, and Elsevier Science Publishing Company, New York, pp 394 (1991)).

The references listed below show different types of surfaces used for reverse phase separations and are hereby incorporated by reference herein in their entireties: CHROMATOGRAPHY, $5^{th}$ edition, Part A: Fundamentals and Techniques, editor: E. Heftmann, Elsevier Science Publishing Company, New York, pp A25 (1992); ADVANCED CHROMATOGRAPHIC AND ELECTROMIGRATION METHODS IN BIOSCIENCES, editor: Z. Deyl, Elsevier Science BV, Amsterdam, The Netherlands, pp 528 (1998); CHROMATOGRAPHY TODAY, Colin F. Poole and Salwa K. Poole, and Elsevier Science Publishing Company, New York, pp 394 (1991).

Ion-pair chromatography media can also function as an extraction media in certain embodiments of the invention. In ion-pair chromatography, the column packing is usually the same as in reversed-phase chromatography; e.g., a $C_8$ or $C_{18}$ silica. The mobile phase is likewise similar to that used in reverse phase chromatography: an aqueous/organic solvent mixture containing a buffer plus a so-called ion-pair reagent. The ion-pair reagent will be positively charged for the retention and separation of sample anions and negatively charged for the retention of sample cations. Typical examples of ion-pair reagents are hexane sulfonate and tetrabutylammonium. The basis of retention in ion-pair chromatography is still controversial, two different processes being possible: (a) adsorption of ion pairs or (b) formation of an in situ ion exchanger. Although these two processes appear somewhat different, they lead to quite similar predictions of retention as a function of experimental conditions. Retention in ion-pair chromatography can be continuously varied from a reversed-phase process to an ion-exchange process. This capability provides a number of practical advantages. For example, variation of the mobile phase composition allows a considerable control over the retention of individual sample ions. This can be used to separate particularly difficult samples, e.g., mixtures of anionic, cationic, and/or neutral molecules (CHROMATOGRAPHY, $5^{th}$ Edition, Part A: Fundamentals And Techniques, editor: E. Heftmann, Elsevier Science Publishing Company, New York, pp A28 (1992)).

The references listed below show different types of groups used for ion-pair chromatography and are hereby incorporated by reference herein in their entireties: Reference: CHROMATOGRAPHY, $5^{th}$ Edition, Part A: Fundamentals and Techniques, editor: E. Heftmann, Elsevier Science Publishing Company, New York, pp A28 (1992); and CHROMATOGRAPHY TODAY, Colin F. Poole and Salwa K. Poole, Elsevier Science Publishing Company, New York, pp 411 (1991).

Normal phase chromatography media can also function as an extraction media in certain embodiments of the invention. In normal phase chromatography, the stationary phase is a high-surface-area polar adsorbent, e.g., silica or a bonded silica with polar surface groups. The mobile phase (a mixture of organic solvents) is less polar than the stationary phase. Consequently, more polar solutes are preferentially retained; there is often little difference in the retention of different homologues or a particular compound class. This has led to the use of normal phase chromatography for so-called compound-class (group-type) separations, where, e.g., alcohols are separated as a group from monoesters and other compound classes. The basis of normal phase chromatography retention is an adsorption/displacement process. Another feature of normal phase chromatography retention is the so-called localization of adsorbed solute and mobile-phase molecules on the stationary-phase surface. Localization refers to the formation of discrete bonds (by dipole/dipole or hydrogen-bonding interactions) between polar sites on the adsorbent and polar substituents in the solute molecule. Localization, in turn, confers a high degree of specificity to the interaction of solute isomers with the adsorbent surface, leading to typically better separations of isomers by normal phase chromatography than by other chromatographic methods (*CHROMATOGRAPHY*, $5^{th}$ edition, Part A: Fundamentals and Techniques, editor: E. Heftmann, Elsevier Science Publishing Company, New York, pp A27 (1992)).

The references listed below show different types of affinity groups used for normal phase chromatography and are hereby incorporated by reference herein in their entireties: CHROMATOGRAPHY, 5$^{th}$ edition, Part A: Fundamentals and Techniques, editor: E. Heftmann, Elsevier Science Publishing Company, New York, pp A27 (1992); and CHROMATOGRAPHY TODAY, Colin F. Poole and Salwa K. Poole, Elsevier Science Publishing Company, New York, pp 375 (1991).

Ion Exchange chromatography media can also function as an extraction media in certain embodiments of the invention. Ion Exchange (IEX) is a mode of chromatography in which ionic substances are separated on cationic or anionic sites of the packing. The surface in ion exchange is usually an organic matrix which is substituted with ionic groups, e.g., sulfonate or trimethylammonium. The mobile phase typically consists of water plus buffer and/or salt. The retention of a solute ion occurs via ion exchange with a mobile phase ion or similar (positive or negative) charge. Ion exchange chromatography is often applied to the separation of acidic or basic samples, whose charge varies with pH. In the simple case of solute molecules bearing a single acidic or basic group, the solute will be present as some mixture of charged and neutral species. The fraction of solute molecules that are ionized then determines retention. In the case of ion exchange, the retention of the uncharged species can be ignored (CHROMATOGRAPHY, 5$^{th}$ Edition, Part A: Fundamentals and Techniques, editor: E. Heftmann, Elsevier Science Publishing Company, New York, pp A28 (1992)). Ion exchange chromatography is one of the oldest and most traditional techniques for separating complex mixtures of proteins.

The references listed below show different types of groups and surfaces used for ion exchange chromatography and are hereby incorporated by reference herein in their entireties; CHROMATOGRAPHY, 5$^{th}$ Edition, Part A: Fundamentals and Techniques, editor: E. Heftmann, Elsevier Science Publishing Company, New York, pp A28 (1992); CHROMATOGRAPHY TODAY, Colin F. Poole and Salwa K. Poole, Elsevier Science Publishing Company, New York, pp 422 (1991); and ADVANCED CHROMATOGRAPHIC AND ELECTROMIGRATION METHODS IN BIOSCIENCES, editor: Z. Deyl, Elsevier Science BV, Amsterdam, The Netherlands, pp 540 (1998).

Hydrophobic Interaction Chromatography media can also function as an extraction media in certain embodiments of the invention. Hydrophobic Interaction Chromatography is widely used for the separation and purification of proteins. During separation, proteins are induced to bind to a weakly hydrophobic stationary phase using a buffered mobile phase of high ionic strength and then selectively desorbed during a decreasing salt concentration gradient. Proteins are usually separated in hydrophobic interaction chromatography according to their degree of hydrophobicity, much as in reversed-phase chromatography, but because of the gentler nature of the separation mechanism, there is a greater probability that they will elute with their conformational structure (biological activity) intact. In reversed-phase chromatography, proteins unfold on the bonded phase surface as a consequence of the high interfacial tension existing between the mobile and the bonded stationary phases. These conditions are minimized in hydrophobic interaction chromatography by using stationary phases of lower hydrophobicity together with totally aqueous mobile phases, in general, since solvent strength is controlled by varying ionic strength rather than by increasing the volume fraction of an organic modifier. Retention and selectivity in hydrophobic interaction chromatography depend substantially on the type of stationary phase. Retention increases for more hydrophobic ligands and with it the possibility of denaturing certain proteins. Some proteins are only satisfactorily handled on hydrophilic stationary phases. The ligand density and structure as well as the hydrophobicity of the stationary phase are the primary stationary phase variables that should be optimized for the separation of individual proteins. Mobile phase parameters that have to be optimized are the salt concentration, salt type, slope of the salt gradient, pH, addition of surfactant or organic modifier and temperature. In the absence of specific binding of the salt to the protein molecule and at relatively high salt concentration in the mobile phase, retention increases linearly with the salt molality and at constant salt concentration with the molal surface tension increment of the salt used in the aqueous mobile phase.

The reference listed below shows different types of groups and surfaces used for hydrophobic interactions and is hereby incorporated by reference herein in its entirety: CHROMATOGRAPHY TODAY, Colin F. Poole and Salwa K. Poole, Elsevier Science Publishing Company, New York, 402 (1991).

Frits

Columns of the invention employ frits having a low pore volume, which contributes to the low dead volume of the columns. The frits of the invention are porous, since it is necessary for fluid to be able to pass through the frit. The frit should have sufficient structural strength so that frit integrity can contain the extraction media in the column. It is desirable that the frit have little or no affinity for chemicals with which it will come into contact during the extraction process, particularly the analyte of interest. In many embodiments of the invention the analyte of interest is a biomolecule, particularly a biological macromolecule. Thus in many embodiments of the invention it desirable to use a frit that has a minimal tendency to bind or otherwise interact with biological macromolecules, particularly proteins, peptides and nucleic acids.

Frits of various pores sizes and pore densities may be used provided the free flow of liquid is possible and the beads are held in place within the extraction media bed.

One frit, i.e., a lower frit, is bonded to and extends across the open channel of the column body. A second frit is bonded to and extends across the open channel between the bottom frit and the open upper end of the column body.

The top frit, bottom frit and channel surface define an extraction media chamber wherein a bed of extraction media is positioned. The frits should be securely attached to the column body and extend across the opening and/or open end so as to completely occlude the channel, thereby substantially confining the bed of extraction media inside the extraction media chamber. In certain embodiments of the invention the bed of extraction media occupies at least 80% of the volume of the extraction media chamber, more preferably 90%, 95%, 99%, or substantially 100% of the volume. In some embodiments the invention the space between the extraction media bed and the upper and lower frits is negligible, i.e., the frits are in substantial contact with upper and lower surfaces of the extraction media bed, holding a well-packed bed of extraction media securely in place.

In some embodiments of the invention the bottom frit is located at the open lower end of the column body. This configuration is shown in the figures and exemplified in the Examples, but is not required, i.e., in some embodiments the bottom frit is located at some distance up the column body from the open lower end. However, in view of the importance of minimizing dead volume in the column it is desirable that the lower frit and extraction media chamber be located at or near the lower end. In some cases this can mean that the bottom frit is attached to the face of the open lower end, as shown in FIGS. 1-10. However, in some cases there can be some portion of the lower end extending beyond the bottom frit, as exemplified by the embodiment depicted in FIG. 11. For the purposes of this invention, so long as the length as this extension is such that it does not substantially introduce dead volume into the extraction column or otherwise adversely impact the function of the column, the bottom frit is considered to be located at the lower end of the column body. In some embodiments of the invention the volume defined by the bottom frit, channel surface, and the face of the open lower end (i.e., the channel volume below the bottom frit) is less than the volume of the extraction media chamber, or less than 10% of the volume of the extraction media chamber, or less than 1% of the volume of the extraction media chamber.

The frits used in the invention are characterized by having a low pore volume. Some embodiments of the invention employ frits having pore volumes of less than 1 microliter (e.g., in the range of 0.015-1 microliter, 0.03-1 microliter, 0.1-1 microliter or 0.5-1 microliter), preferably less than 0.5 microliter (e.g., in the range of 0.015-0.5 microliter, 0.03-0.5 microliter or 0.1-0.5 microliter), less than 0.1 microliter (e.g., in the range of 0.015-0.1 microliter or 0.03-0.1 microliter) or less than 0.03 microliters (e.g., in the range of 0.015-0.03 microliter).

Frits of the invention preferably have pore openings or mesh openings of a size in the range of about 5-100 µm, more preferably 10-100 µm, and still more preferably 15-50 µm, e.g, about 43 µm. The performance of the column is typically enhanced by the use of frits having pore or mesh openings sufficiently large so as to minimize the resistance to flow. The use of membrane screens as described herein typically provide this low resistance to flow and hence better flow rates, reduced back pressure and minimal distortion of the bed of extraction media. The pore or mesh openings of course should not be so large that they are unable to adequately contain the extraction media in the chamber.

The frits used in the practice of the invention are characterized by having a low pore volume relative to the interstitial volume of the bed of extraction media contained by the frit. Thus, in certain embodiments of the invention the frit pore volume is equal to 10% or less of the interstitial volume of the bed of extraction media (e.g., in the range 0.1-10%, 0.25-10%, 1-10% or 5-10% of the interstitial volume), more preferably 5% or less of the interstitial volume of the bed of extraction media (e.g., in the range 0.1-5%, 0.25-5% or 1-5% of the interstitial volume), and still more preferably 1% or less of the interstitial volume of the bed of extraction media (e.g., in the range 0.1-1% or 0.25-0% of the interstitial volume).

The pore density will allow flow of the liquid through the membrane and is preferably 10% and higher to increase the flow rate that is possible and to reduce the time needed to process the sample.

Some embodiments of the invention employ a thin frit, preferably less than 350 µm in thickness (e.g., in the range of 20-350 µm, 40-350 µm, or 50-350 µm), more preferably less than 200 µm in thickness (e.g., in the range of 20-200 µm, 40-200 µm, or 50-200 µm), more preferably less than 100 µm in thickness (e.g., in the range of 20-100 µm, 40-100 µm, or 50-100 µm), and most preferably less than 75 µm in thickness (e.g., in the range of 20-75 µm, 40-75 µm, or 50-75 µm).

Some embodiments of the invention employ a membrane screen as the frit. The membrane screen should be strong enough to not only contain the extraction media in the column bed, but also to avoid becoming detached or punctured during the actual packing of the media into the column bed. Membranes can be fragile, and in some embodiments must be contained in a framework to maintain their integrity during use. However, it is desirable to use a membrane of sufficient strength such that it can be used without reliance on such a framework. The membrane screen should also be flexible so that it can conform to the column bed. This flexibility is advantageous ins the packing process as it allows the membrane screen to conform to the bed of extraction media, resulting in a reduction in dead volume.

Preferably the membrane is a woven or non-woven mesh of fibers that may be a mesh weave, a random orientated mat of fibers i.e. a "polymer paper", a spunbonded mesh, an etched or "pore drilled" paper or membrane such as nuclear track etched membrane or an electrolytic mesh (see, e.g., 5,556, 598). The membrane may be polymer, glass, or metal provided the membrane is low dead volume, allows movement of the various sample and processing liquids through the column bed, may be attached to the column body, is strong enough to withstand the bed packing process, is strong enough to hold the column bed of beads, and does not interfere with the extraction process i.e. does not adsorb or denature the sample molecules.

The frit can be attached to the column body by any means which results in a stable attachment. For example, the screen can be bonded to the column body through welding or gluing. Gluing can be done with any suitable glue, e.g., silicone, cyanoacrylate glue, epoxy glue, and the like. The glue or weld joint must have the strength required to withstand the process of packing the bed of extraction media and to contain the extraction media with the chamber. For glue joints, a glue should be selected employed that does not adsorb or denature the sample molecules.

Alternatively, a frit can be attached by means of an annular pip, as described in U.S. Pat. No. 5,833,927. This mode of attachment is particularly suited to embodiment where the frit is a membrane screen.

The frits of the invention, e.g., a membrane screen, can be made from any material that has the required physical properties as described herein. Examples of suitable materials include nylon, polyester, polyamide, polycarbonate, cellulose, polyethylene, nitrocellulose, cellulose acetate, polyvinylidine difluoride, polytetrafluoroethylene (PTFE), polypropylene and glass. A specific example of a membrane screen is the 43 µm pore size Spectra/Mesh® polyester mesh material which is available from Spectrum Labs (Ranch Dominguez, Calif., PN 145837).

Extraction Column Assembly

The extraction columns of the invention can be constructed by a variety of methods using the teaching supplied herein. In some embodiments the extraction column can be constructed by the engagement (i.e., attachment) of upper and lower tubular members that combine to form the extraction column. Examples of this mode of column construction are described in the Examples and depicted in the figures.

Figure 2:
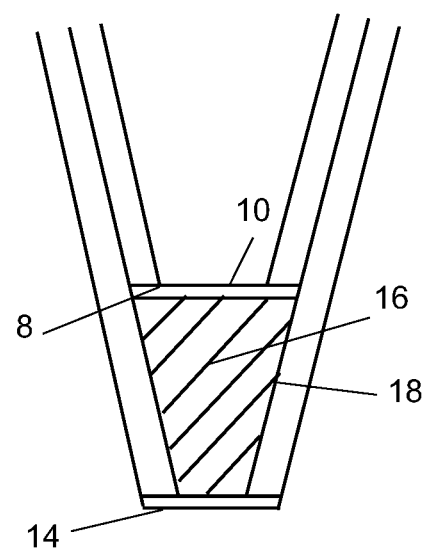
FIG. 2 is an enlarged view of the extraction column of FIG. 1.

For example, an embodiment of the invention wherein in the two tubular members are sections of pipette tips is depicted in FIG. 1 (FIG. 2 is an enlarged view of the open lower end and extraction media chamber of the column). This embodiment is constructed from a frustoconical upper tubular member 2 and a frustoconical lower tubular member 3 engaged therewith. The engaging end 4 of the upper tubular member has a tapered bore that matches the tapered external surfaced of the engaging end 6 of the lower tubular member, the engaging end of the lower tubular member receiving the engaging end of the upper tubular member in a telescoping relation. The tapered bore engages the tapered external surface snugly so as to form a good seal in the assembled column.

A membrane screen 10 is bonded to and extends across the tip of the engaging end of the upper tubular member and constitutes the upper frit of the extraction column. Another membrane screen 14 is bonded to and extends across the tip of the lower tubular member and constitutes the lower frit of the extraction column. The extraction media chamber 16 is defined by the membrane screens 10 and 14 and the channel surface 18, and is packed with extraction media 20.

The pore volume of the membrane screens 10 and 14 is low to minimize the dead volume of the column. The sample and desorption solution can pass directly from the vial or reservoir into the bed of extraction media. The low dead volume permits desorption of the analyte into the smallest possible desorption volume, thereby maximizing analyte concentration.

The volume of the extraction media chamber 16 is variable and can be adjusted by changing the depth to which the upper tubular member engaging end extends into the lower tubular member, as determined by the relative dimensions of the tapered bore and tapered external surface.

The sealing of the upper tubular member to the lower tubular in this embodiment is achieved by the friction of a press fit, but could alternatively be achieved by welding, gluing or similar sealing methods.

Figure 3:
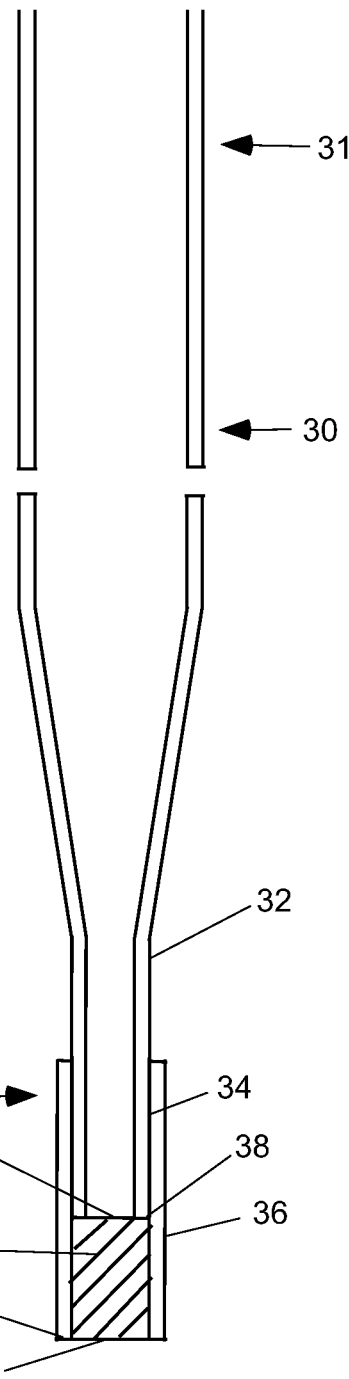
FIG. 3 depicts an embodiment of the invention where the extraction column is constructed from two cylindrical members.

FIG. 3 depicts an embodiment of the invention comprising an upper and lower tubular member engaged in a telescoping relation that does not rely on a tapered fit. Instead, in this embodiment the engaging ends 34 and 35 are cylindrical, with the outside diameter of 34 matching the inside diameter of 35, so that he concentric engaging end form a snug fit. The engaging ends are sealed through a press fit, welding, gluing or similar sealing methods. The volume of the extraction bed can be varied by changing how far the length of the engaging end 34 extends into engaging end 35. Note that the diameter of the upper tubular member 30 is variable, in this case it is wider at the upper open end 31 and tapers down to the narrower engaging end 34. This design allows for a larger volume in the column channel above the extraction media, thereby facilitating the processing of larger sample volumes and wash volumes. The size and shape of the upper open end can be adapted to conform to a pump used in connection with the column. For example, upper open end 31 can be tapered outward to form a better friction fit with a pump such as a pipettor or syringe.

A membrane screen 40 is bonded to and extends across the tip 38 of engaging end 34 and constitutes the upper frit of the extraction column. Another membrane screen 44 is bonded to and extends across the tip 42 of the lower tubular member 36 and constitutes the lower frit of the extraction column. The extraction media chamber 46 is defined by the membrane screens 40 and 44 and the open interior channel of lower tubular member 36, and is packed with extraction media 48.

Figure 4:
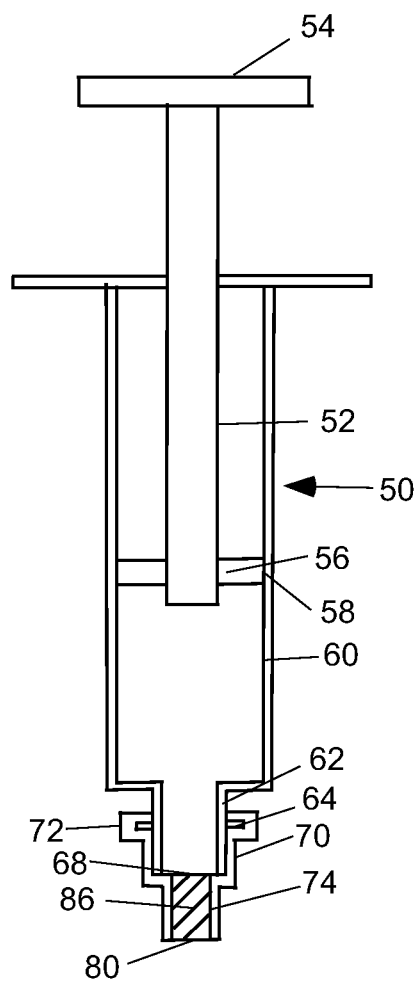
FIG. 4 depicts a syringe pump embodiment of the invention with a cylindrical bed of solid phase media in the tip.
Figure 5:
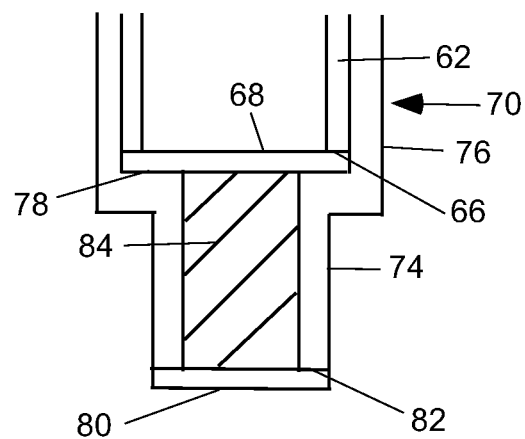
FIG. 5 is an enlarged view of the extraction column element of the syringe pump embodiment of FIG. 4.

FIG. 4 is a syringe pump embodiment of the invention with a cylindrical bed of extraction media in the tip, and FIG. 5 is an enlargement of the top of the syringe pump embodiment of FIG. 4. These figures show a low dead volume column based on using a disposable syringe and column body. Instead of a pipettor, a disposable syringe is used to pump and contain the sample.

The upper portion of this embodiment constitutes a syringe pump with a barrel 50 into which a plunger 52 is positioned for movement along the central axis of the barrel. A manual actuator tab 54 is secured to the top of the plunger 52. A concentric sealing ring 56 is secured to the lower end of the plunger 52. The outer surface 58 of the concentric sealing ring 56 forms a sealing engagement with the inner surface 60 of the barrel 50 so that movement of the plunger 52 and sealing ring 56 up or down in the barrel moves liquid up or down the barrel.

The lower end of the barrel 50 is connected to an inner cylinder 62 having a projection 64 for engaging a Luer adapter. The bottom edge 66 of the inner cylinder 62 has a membrane screen 68 secured thereto. The inner cylinder 62 slides in an outer sleeve 70 with a conventional Luer adaptor 72 at its upper end. The lower segment 74 of the outer sleeve 70 has a diameter smaller than the upper portion 76, outer sleeve 70 forming a ledge 78 positioned for abutment with the lower end 66 and membrane screen 68. A membrane screen 80 is secured to the lower end 82 of the lower segment 74. The extraction media chamber 84 is defined by the upper and lower membrane screens 68 and 80 and the inner channel surface of the lower segment 74. The extraction beads 86 are positioned in the extraction media chamber 84. The volume of extraction media chamber 84 can be adjusted by changing the length of the lower segment 74.

Other embodiments of the invention exemplifying different methods of construction are also described in the examples.

Pump

In using the extraction columns of the invention a pump is attached to the upper open end of the column and used to aspirated and discharge the sample from the column. The pump can take any of a variety of forms, so long as it is capable of generating a negative internal column pressure to aspirate a fluid into the column channel through the open lower end. In some embodiments of the invention the pump is also able to generate a positive internal column pressure to discharge fluid out of the open lower end. Alternatively, other methods can be used for discharging solution from the column, e.g., centrifugation.

The pump should be sufficiently strong so as to be able to draw a desired sample solution, wash solution and/or desorption solvent through the bed of extraction media.

In some embodiments of the invention the pump is capable of controlling the volume of fluid aspirated and/or discharged from the column, e.g., a pipettor. This allows for the metered intake and outtake of solvents, which facilitates more precise elution volumes to maximize sample recovery and concentration.

Non-limiting examples of suitable pumps include a pipettor, syringe, peristaltic pump, electrokinetic pump, or an induction based fluidics pump.

III. Methods for Using the Extraction Columns

Extraction columns of the invention should be stored under conditions that preserve the integrity of the extraction media. For example, columns containing agarose- or sepharose-based extraction media should be stored under cold conditions (e.g., 4 degrees Celsius) and in the presence of 0.01 percent sodium azide or 20 percent ethanol.

The sample solution can be any solution containing an analyte of interest. The invention is particularly useful for extraction and purification of biological molecules, hence the sample solution is often of biological origin, e.g., a cell lysate. In one embodiment of the invention the sample solution is a hybridoma cell culture supernatant.

Prior to extraction, a conditioning step may be employed. If analyte extraction is incomplete in a single pass, the sample solution can be passed back and forth through the media several times. An optional wash step between the extraction and desorption steps can also improve the purity of the final product. Typically water or a buffer is used for the wash solution. The wash solution is preferably one that will remove unwanted contaminants with a minimal desorption of the analyte of interest.

The volume of desorption solvent used can be very small, approximating the interstitial volume of the bed of extraction media. In certain embodiments of the invention the amount of desorption solvent used is less than 10-fold greater than the interstitial volume of the bed of extraction media, more preferably less than 5-fold greater than the interstitial volume of the bed of extraction media, still more preferably less than 3-fold greater than the interstitial volume of the bed of extraction media, still more preferably less than 2-fold greater than the interstitial volume of the bed of extraction media, and most preferably is equal to or less than the interstitial volume of the bed of extraction media.

The desorption solvent will vary depending upon the nature of the analyte and extraction media. For example, where the analyte is a His-tagged protein and the extraction media an IMAC resin, the desorption solution will contain imidazole or the like to release the protein from the resin. In some cases desorption is achieved by a change in pH or ionic strength, e.g., by using low pH or high ionic strength desorption solution. A suitable desorption solution can be arrived at using available knowledge by one of skill in the art.

In one embodiment, the extraction column may be used for multidimensional stepwise solid phase extraction of isotope-coded affinity tagged (ICAT) peptides. The fractions are collected on the basis of increasing ionic strength or pH, and can be processed in the affinity separation dimension described below, but with suitable adjustments being made for larger sample volumes being introduced into the affinity capillary and/or possible differences in pH. In certain instances the fractions collected from the avidin affinity column may be processed further for cleavage of the affinity tag from the isotope-coding region, prior to separation in the reversed-phase separation dimension described below.

The cleavage can be performed directly upon the collected fraction by photocleavage as described in Huilin Zhou, et al., *Nature Biotech.*, 19:512 (2002), or acid cleavage with TFA-triethylsilane as described in Brian Williamson, et al., Proceedings of the 50$^{th}$ ASMS Conference on Mass Spectrometry and Allied Topics, Orlando, Fla., Jun. 2-6, 2002, Orlando, Fla., Poster # WPA023, or by evaporating the collected fraction to dryness by standard means and adding TFA-triethylsilane reagent to achieve acid cleavage as described in Williamson, et al, 50$^{th}$ ASMS Conference Proceedings, Jun. 2-6, 2002, Orlando, Fla., Poster # WPA023 (2002).

In instances where the peptide mixture generated by the release, labeling and proteolysis is not excessively complex, it may be possible to bypass the ion-exchange separation dimension and proceed directly to the affinity separation dimension. An example of bypassing the ion-exchange separation dimension is given in LC Packings/Dionex' Application Note, "2D Analysis of Isotope Coded Affinity Tag (ICAT) Labeled Proteins," Application Note UltiMate Capillary and Nano LC System, Proteomics #09. However, if this strategy is applied it is advised that some suitable means be applied for removal of the unincorporated ICAT tags prior to introducing the sample to the monomeric avidin column, which would otherwise be removed in the ion-exchange separation dimension.

In certain instances it may be possible to bypass the ion-exchange separation and affinity separation dimensions and proceed directly from the sample protein release, lysis and labeling step (i.e. the first step described at the beginning of this example) to the reversed-phase separation dimension, such as when solid-phase isotope-coded tagging reagents are being utilized as described in Huilin Zhou, et al., *Nature Biotech.*, 19:512 (2002); in this case the cleavage of the isotope-coded peptide from the solid-phase support can be achieved by photocleavage as described in Huilin Zhou, et al., *Nature Biotech.*, 19:512 (2002) or by acid cleavage as described in Brian Williamson, et al., Proceedings of the 50$^{th}$ ASMS Conference on Mass Spectrometry and Allied Topics, Orlando, Fla., Jun. 2-6, 2002, Orlando, Fla., Poster # WPA023.

The device, apparatus and method of this invention can be used to prepare materials for protein chips, DNA chips or other biochips.

Protein chips dynamics can be represented by the following equation:

$$A+B=AB$$

AB is capable of generating an analytical signal, where A is the chip-bound moiety and B is its cognate binder introduced to the chip. An assumption of specific interactions is always assumed. Binding events other than "AB" can have the appearance of AB, the variance being caused by non-A (i.e. contaminating) moieties having some affinity for B, non-B (i.e. contaminating) moieties having some affinity for A, or a combinations of the two; any of these events will have the appearance of a true AB event. This characteristic will define the success or failure of a particular protein chip experiment, and is the most trivialized or ignored aspects of the technology.

For some non-protein chips (specifically DNA chips), the A groups do not require purification or enrichment since they are synthesized in place, or are amplified via PCR and spotted. With the exception of very short peptides, the structural complexity of proteins will not allow for on-chip synthesis of A. Therefore, preparation of A materials for use within protein chips will place a premium on the purity of the material. In addition, the A materials will often need to be highly enriched so as to provide maximum opportunity for AB to occur.

Protein chips are characterized by having small volumes of "A" applied to the surface. The volumes are often on the order of 10 mL or less for each spot. Since many proteins are difficult and/or expensive to prepare, the ability to purify and enrich at scales on par with the spots would significantly reduce waste. It would also allow for "just-in-time" purification, so that the chip is prepared just as the protein is being purified.

Different materials are brought to the chip as A, and each material require purification and/or enrichment. Examples of these materials are antibodies (i.e. IgG, IgY, etc) as affinity molecules, general affinity proteins (i.e. scFvs, Fabs, affibodies, peptides, etc) as affinity molecules, other proteins that are being screened for general affinity characteristics, and nucleic acids/(photo) aptamers as affinity molecules, for example.

Different means of attaching A to chip surfaces, and each will require purification and enrichment procedures that are compatible with the attachment chemistry. Examples of attachment chemistry include direct/passive immobilization to protein chip substrates, and these can become covalent in cases of native thiols associating with gold surfaces, as one example. Covalent attachment is another method of attachment of functional groups at chip surface, and these can be self-assembled monolayers with and without additional groups, immobilized hydrogel, and the like. Non-covalent/affinity attachment to functional groups/ligands at chip surface is another method of attachment; examples of this method are ProA or ProG for IgGs, phenyl(di)boronic acid with salicylhydroxamic acid groups; streptavidin monolayers with biotinylation of native lysines/cysteines, and the like.

The samples or analyte to be brought to the chip can be varied in composition and mode of interaction with A.

There is more than one way to achieve specific AB interactions through the manipulation of B. One means is to remove potentially interfering non-B contaminants by their specific removal, provided these contaminants are sufficiently well-defined such as albumin, fibrin, etc.

Another means is the removal of non-B contaminants by trapping B (either individually or as a class), removing contaminants by washing, and releasing B. This simultaneously allows for enrichment of B, thus enhancing the sensitivity for the AB event.

Just as the scale of the chip is very small, there are opportunities to make the scale of the sample small—therefore allowing for analysis of very small samples. Since samples are precious materials, the scale of purification and enrichment would allow for this to occur. As with chip preparation, this can occur in a "just-in-time" manner.

The detection event requires some manner of A interacting with B, so the central player in the detection event (since it isn't part of the protein chip itself) is B. The means of detecting the presence of B (or, B-like substances described above) are varied and can include label-free detection of B (or B-like substances) interacting with A such as surface plasmon resonance imaging as practiced by HTS Biosystems—grating-coupled SPR or BiaCore—prism or Kretschmann-based SPR, or Micro-cantilever detection schemes as practiced by Protiveris.

The detection means can include physical labeling of B (or B-like substances) interacting with A, followed by spatial imaging of AB pair (i.e. Cy3/Cy5 differential labeling with standard fluorescent imaging as practiced by BD Biosciences Clontech, radioactive ATP labeling of kinase substrates with autoradiography imaging as practiced by Jerini or other suitable imaging techniques. In the case of fluorescent tagging, one can achieve higher sensitivity with fluorescent waveguide imaging as practiced by ZeptoSens.

The detection means can also include interaction of AB complex with a third B-specific affinity partner C, where C is capable of generating a signal by being fluorescently tagged, or is tagged with a group that allows a chemical reaction to occur at that location (such as generation of a fluorescent moiety, direct generation of light, etc). Detection of this AB-C binding event can occur via fluorescent imaging as practiced by Zyomyx and SomaLogic, chemiluminescence imaging as practiced by HTS Biosystems and Hypromatrix, fluorescent imaging via waveguide technology, or other suitable detection means.

Arrayers are instruments for spotting nucleic acids, proteins or other reagent onto chips that are used for molecular biology research or diagnostic work. The arrayers can be used both in the manufacture of the chips and in the use of the chip. In manufacturing, an arrayer can be used to transport the chemical reactants to specific spots on the chip. This may be a multi-step process as the chemical complex used for detection is built at each particular spot in the array.

Each process can require sample preparation. In some cases, DNA is purified and deposited to a surface on a chip. Then samples containing complementary DNA or RNA are reacted with the chip. Before the samples can be reacted, the nucleic acid is purified away from the other materials (proteins, particulate, carbohydrates, etc.) found in the samples. In other cases, protein chips may be manufactured by depositing specific proteins in an array. Then samples containing proteins can be reacted with various array sites to measure protein/protein interactions.

In application of mass spectrometry for the analysis of biomolecules, the molecules must be transferred from the liquid or solid phases to gas phase and to vacuum phase. Since most biomolecules are both large and fragile, the most effective methods for their transfer to the vacuum phase are matrix-assisted laser desorption ionization (MALDI) or electrospray ionization (ESI). Mass spectrometry provides essentially two methods for analyzing proteins: bottom up and top down analysis. In bottom up analysis, the protein is manipulated and broken up in a controlled manner (usually through an enzymatic digestion process), analyzed, and then reassembled using the data from the various parts. Top down analysis works with the whole protein, optionally using an ion source to break apart the protein and determine the identity of the protein.

While both methods may require long mass spectrometer analysis times, top down approaches usually require the longest time. Under ideal cases, a static sample is measured and parameters on the manner in which the source is directed or implemented. The methods in which the data are analyzed are varied to perform a full analysis of the protein.

Many sample introduction methods introduce samples "on-the-fly." The sample is introduced from an HPLC column as continuous flow into the nozzle of the electrospray ionization (ESI) source. In order to introduce samples so that top down analysis can be implemented, the flow of the sample may be slowed. The method is called peak parking. In this way, the sample residence time can be increased by a factor of 10 or greater increasing the sensitivity of the analysis by a factor of 8 or greater. However, this method is still inflexible and inadequate because the analysis must still be performed quickly—often more quickly than the instrument is capable of performing.

This is also true for introduction of samples from a solid phase extraction device. One may introduce the entire sample before the analysis is completed. It is much better to introduce a discrete uniform sample into the mass spectrometer. In this way, the mass spectrometry method and procedure can be adapted to the sample in the best manner.

This can be accomplished by using an apparatus where the desorbed material from an open tube extraction device is deposited directly into an electrospray nozzle.

MALDI is commonly interfaced to time of flight (TOF) mass spectrometers (MALDI-TOF) and ESI is interfaced to quadrupole, ion trap and TOF mass analyzers. Both MALDI and ESI approaches are useful for determining the full masses of proteins and peptides in mixtures, before and after purification and to induce fragmentation of peptides for ms/ms analysis. Modern mass spectrometry is accurate enough to be useful for evaluating the correct translation or chemical synthesis of biomolecules. Any deviation of the observed mass of the sample from its calculated mass indicates incorrect synthesis or the presence of post-translational or chemical modifications. Biomolecules can be purposely fragmented in the mass spectrometer and the masses of the resulting fragments can be accurately determined. The patterns of such fragment masses are useful for ms/ms sequencing of the peptides and their identification in the data banks.

Electrospray is performed by mixing the sample with volatile acid and organic solvent and infusing it through a conductive needle charged with high voltage. The charged droplets that are sprayed (or ejected) from the needle end, are directed into the mass spectrometer, and are dried up by heat and vacuum as they fly in. After the drops dry, the remaining charged molecules are directed by electromagnetic lenses into the mass detector and mass analyzed. Electrospray mass spectrometry can be used to determine the masses of different molecules, from small peptides to intact large proteins. Even though the mass-range of the currently available instruments is only 2000 to 10000 mass unit, most proteins become multi-charged during the electrospray step and since the instrument measures the mass to charge ratio (m/z) of the molecules, most proteins are sufficiently charged to have an m/z that is within the mass range. To calculate the full mass of the protein from the different m/z measured, a deconvolution is performed, returning the full mass of the proteins.

For MALDI-TOF the proteins are deposited on metal targets, as co-crystallized with an organic matrix. The samples are dried and inserted into the mass spectrometer. After vacuum is established, the matrix crystals absorb the light energy from short flashes of a high-energy laser. The matrix rapidly sublimes, carrying with it the biomolecule into the vacuum phase. The sample and matrix plume enter a strong electromagnetic field that accelerate the charged molecules into a free flight zone where they fly until they hit a detector located at its far end. The mass of the protein can be calculated from its flight time. Accurate determination of the masses is obtained by the flight time to that of a standard of known mass. The flight time is proportional to the log of mass of the protein and the larger proteins fly slower and reach the detector later.

All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless so specified.

EXAMPLES

The following preparations and examples are given to enable those skilled in the art to more clearly understand and practice the present invention. They should not be construed as limiting the scope of the invention, but merely as being illustrative and representative thereof.

Example 1

Preparation of an Extraction Column Body from Pipette Tips

Figure 6:
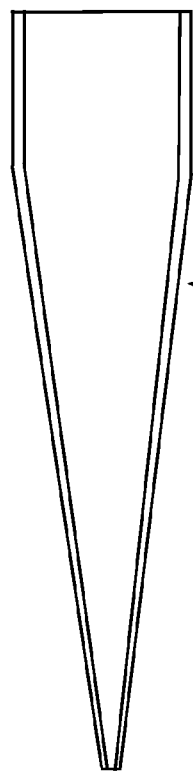
FIGS. 6-10 show successive stages in the construction of the embodiment depicted in FIGS. 1 and 2.

Two 1000 µL polypropylene pipette tips of the design shown in FIG. 6 (VWR, Brisbane, Calif., PN 53508-987) were used to construct one extraction column. In this example, two extraction columns were constructed: a 10 µL bed volume and 20 µL bed volume. To construct a column, various components were made by inserting the tips into several custom aluminum cutting tools and cutting the excess material extending out of the tool with a razor blade to give specified column lengths and diameters.

Figure 7:
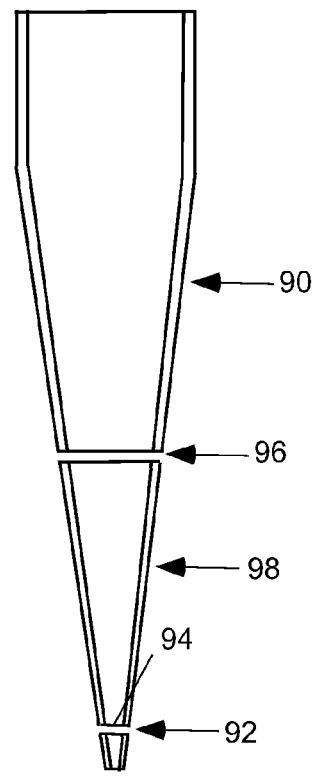

Referring to FIG. 7, the first cut 92 was made to the tip 92 of a pipette tube 90 to form a 1.25 mm inside diameter hole 94 on the lower column body, and a second cut 96 was made to form a lower column body segment 98 having a length of 15.0 mm.

Figure 8:
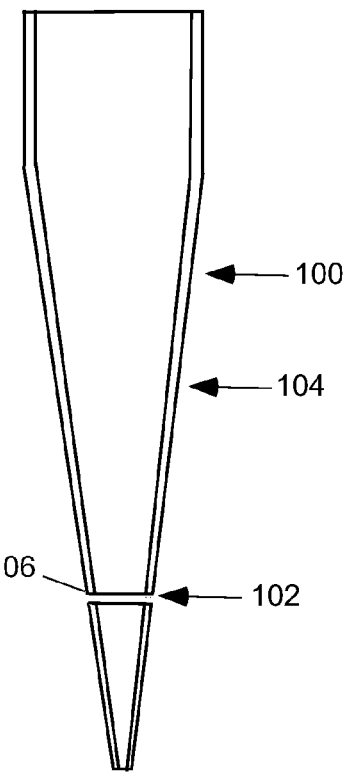

Referring to FIG. 8, a cut 102 was made to the separate pipette tip 100 to form the upper column body 104. To make a 10 µL bed volume column, the cut 102 was made to provide a tip 106 outside diameter of 2.09 mm so that when the upper body was inserted into the lower body, the column height of the solid phase media bed 114 (FIG. 10) was 4.5 mm. To make a 20 µL bed volume column, the cut 102 was made to provide a tip outside diameter of 2.55 mm cut so that when the upper body was inserted into the lower body, the column height of the solid phase media bed 114 (FIG. 10) was 7.0 mm.

Figure 9:
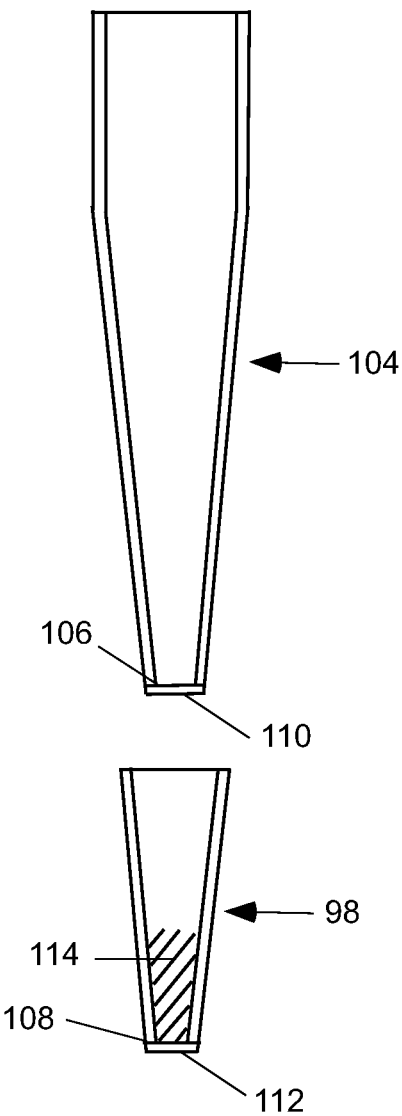

Referring to FIG. 9, a 43 µm pore size Spectra/Mesh® polyester mesh material (Spectrum Labs, Ranch Dominguez, Calif., PN 145837) was cut into discs by a circular cutting tool (Pace Punches, Inc., Irvine, Calif.) and attached to the ends 106 and 108 upper column and lower column bodies to form the membrane screens 110 and 112. The membrane screens were attached using PLASTIX® cyanoacrylate glue (Loctite, Inc., Avon, Ohio). The glue was applied to the polypropylene body and then pressed onto the membrane screen material. Using a razor blade, excess mesh material was removed around the outside perimeter of each column body end.

Figure 10:
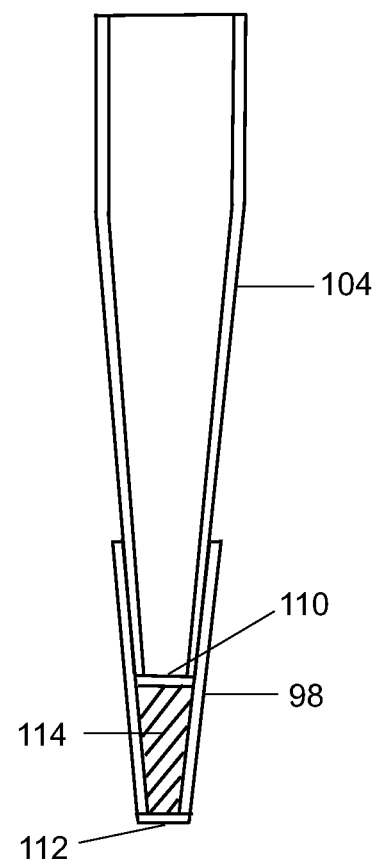

Referring to FIG. 10, the upper column body 104 is inserted into the top of the lower column body segment 98 and pressed downward to compact the solid phase media bed 114 to eliminate excess dead volume above the top of the bed.

Example 2

Preparation of SEPHAROSE™ Protein G and MEP HYPERCEL™ Extraction Columns

Referring to FIG. 9, a suspension of Protein G SEPHAROSE™ 4 Fast Flow, 45-165 µm particle size, (Amersham Biosciences, Piscataway, N.J., PN 17-0618-01) in water/ethanol was prepared, and an appropriate amount of material 114 was pipetted into the lower column body 98.

Referring to FIG. 10, the upper column body 104 was pushed into the lower column body 98 so that no dead space was left at the top of the bed 114, that is, at the top of the column bed. Care was taken so that a seal was formed between the upper and lower column bodies 104 and 98 while retaining the integrity of the membrane screen bonding to the column bodies.

Several tips of 10 µL and 20 µL bed volumes were prepared. Several MEP (Mercapto-Ethyl-Pyridine) HYPERCEL™ (Ciphergen, Fremont, Calif., PN 12035-010) extraction columns were prepared using the same procedure. MEP HyperCel™ resin is a sorbent, 80-100 µm particle size, designed for the capture and purification of monoclonal and polyclonal antibodies. The extraction columns were stored with an aqueous solution of 0.01% sodium azide in a refrigerator before use.

Example 3

Purification of anti-leptin monoclonal antibody IgG with 10 µL and 20 µL Bed Volume Protein G SEPHAROSE™ Extraction Columns A Protein G SEPHAROSE™ 4 Fast Flow (Amersham Biosciences, Piscataway, N.J., PN 17-0618-01) extraction column was prepared as described in Example 2.

Five hundred µL serum-free media (HTS Biosystems, Hopkinton, Mass.) containing IgG (HTS Biosystems, Hopkinton, Mass.) of interest was combined with 500 µL standard PBS buffer. The resulting 1 mL sample was pulled into the pipette tip, through the Protein G packed bed at a flow rate of approximately 1 mL/min) or roughly 15 cm/min). The sample was then pushed out to waste at the same approximate flow rate. Extraneous buffer was removed from the bed by pulling 1 mL of deionized water into the pipette column at about 1 mL/min and pushing it out at about 1 mL/min. The water was pushed out as much as possible to achieve as dry of a column bed as is possible. The IgG was eluted from the column bed by drawing up an appropriate eluent volume of 100 mM glycine-.HCl, pH 2.5 (20 μL eluent in the case of a 20 μL bed volume, 15 μL eluent in the case of a 10 μL bed volume). When the eluent was fully drawn into the bed, it was "pumped" back and forth through the bed five or six times, and the IgG-containing eluent was then fully expelled from the bed. The eluted material was then neutralized with 100 mM $NaH_2PO_4$/ 100 mM $Na_2HPO_4$ (5 μL neutralization buffer in the case of a 20 μL bed volume, 4 μL neutralization buffer in the case of a 10 μL bed volume). The purified and enriched antibodies were then ready for arraying.

Example 4

Purification of Anti-Leptin Monoclonal Antibody IgG with 10 μL and 20 μL Bed Volume Protein G SEPHAROSE™ Extraction Columns A Protein G SEPHAROSE™ 4 Fast Flow (Amersham Biosciences, Piscataway, N.J., PN 17-0618-01) extraction column was prepared as described in Example 2.

Five hundred μL serum-free media (HTS Biosystems, Hopkinton, Mass.) containing IgG (HTS Biosystems, Hopkinton, Mass.) of interest was combined with 500 μL standard PBS buffer. The resulting 1 mL sample was pulled into the pipette tip, through the Protein G packed bed at a flow rate of approximately 1 mL/min (or roughly 150 cm/min linear velocity). The sample was then pushed out to waste at the same approximate flow rate. Extraneous buffer was removed form the bed by pulling 1 mL of deionized water into the pipette column at about 1 mL/min and pushing it out at about 1 mL/min. The water was pushed out as much as possible to achieve as dry of a column bed as is possible. The IgG was eluted from the column bed by drawing up an appropriate eluent volume of 10 mM phosphoric acid ($H_3PO_4$), pH 2.5 (20 μL eluent in the case of a 20 μL bed volume, 15 μL eluent in the case of a 10 μL bed volume). When the eluent was fully drawn into the bed, it was "pumped" back and forth through the bed five or six times, and the IgG-containing eluent is then fully expelled from the bed. The eluted material was then neutralized with a specially designed phosphate neutralizing buffer of 100 mM $H_2NaPO_4$/100 mM $HNa_2PO_4$, pH 7.5 (5 μL neutralization buffer in the case of a 20 μL bed volume, 4 μL neutralization buffer in the case of a 10 μL bed volume). The purified and enriched antibodies were then ready for arraying.

Example 5

Analysis of Purified IgG with Grating-Coupled Surface Plasmon Resonance (GC-SPR)

The anti-leptin monoclonal antibody IgG purified sample from Example 4 was analyzed with GC-SPR. The system used for analysis was a FLEX CHIP™ Kinetic Analysis System (HTS Biosystems, Hopkinton, Mass.), which consists of a plastic optical grating coated with a thin layer of gold on to which an array of biomolecules is immobilized. To immobilize the purified IgG, the gold-coated grating was cleaned thoroughly with EtOH (10-20 seconds under a stream of EtOH). The gold-coated grating was then immersed in a 1 mM solution of 11-mercaptoundecanoic acid (MUA) in EtOH for 1 hour to allow for the formation of a self-assembled monolayer. The surface was rinsed thoroughly with EtOH and ultra-pure water, and dried under a stream of nitrogen. A fresh solution of 75 mM EDC (1-Ethyl-3-(3-Dimethylaminopropyl) carbodiimide hydrochloride) and 15 mM Sulfo-NHS (N-Hydroxysulfo-succinimide) was prepared in water. An aliquot of the EDC/NHS solution was delivered to the surface and allowed to react for 20-30 minutes, and the surface was then rinsed thoroughly with ultra-pure water. An aliquot of 1 mg/mL Protein A/G in PBS, pH 7.4 was delivered to the surface. The surface was placed in a humid environment and allowed to react for 1-2 hours. The surface was allowed to air dry, was rinsed with ultra-pure water and then dried under a stream of nitrogen. Immediately prior to arraying of the IgGs, the surface was rehydrated by placing in a humidified chamber, such as available with commercial arraying systems (e.g. Cartesian MicroSys synQUAD System). The purified anti-leptin IgG was arrayed onto the surface as described previously (J. Brockman, et al, "Grating-Coupled SPR: A Platform for Rapid, Label-free, Array-Based Affinity Screening of Fabs and Mabs", 12$^{th}$ Annual Antibody Engineering Conference, Dec. 2-6, 2001, San Diego, Calif.) and the surface was introduced to the HTS Biosystems FLEX CHIP System. 150 nM leptin in PBS, pH 7.4 was introduced to the surface through the FLEX CHIP System, and real-time binding signals were collected as described previously (ibid.). These real-time binding signals were mathematically processed in a manner described previously (D. Myszka, "Kinetic analysis of macromolecular interactions using surface plasmon resonance biosensors", Current Opinion in Biotechnology, 1997, Vol 8, pp. 50-57) for extraction of the association rate ($k_a$), dissociation rate ($k_d$), and the dissociation affinity constant ($K_d=k_d/k_a$). The kinetic data obtained is shown in Table II below.

TABLE II

| | | Serum-free medium | PBS |
|---|---|---|---|
| No processing (Adequate [IgG]) | Mean $K_d$ | 18 nM | 3.2 nM |
| | Starting [IgG] | 500 μg/mL | 500 μg/mL |
| With processing (Insufficient [IgG] | Mean $K_d$ | 6.6 nM | 5.9 nM* |
| | Starting [IgG] | 20 μg/mL | 500 μg/mL* |

*500 μg/mL IgG in PBS was not processed, but was included in the SPR analysis for the purpose of comparing dissociation affinity constants calculated for each The first set of data for "No processing" indicates that when sufficient IgG is present for detection (500 μg/mL) that the constituents from the serum-free medium can contribute to inaccuracies. These data indicate for equal concentrations of IgG spotted within an experiment, the calculated dissociation affinity constant can be nearly six-fold different from one another (18 nM vs. 3.2 nM). This can only be a result of components within the serum-free medium being co-arrayed with the IgG, since the concentration and composition of IgG is identical for each sample. Therefore, there is a demonstrated need for removal of any extraneous components prior to arraying, which is independent of IgG concentration.

The second set of data for "With processing" indicates that when insufficient IgG quantities are present for detection (20 μg/mL) that sample processing not only allows for generation of sufficient processable signals, but also eliminates the inaccuracies generated from extraneous components. These data indicate that the dissociation affinity constants are virtually identical for 500 μg/mL purified IgG in PBS (unprocessed) as those calculated from 20 μg/mL IgG in serum-free medium once processed with the current invention (5.9 nM vs. 6.6 nM).

Example 6

Purification of Nucleic Acids with an Extraction Column

Columns from Example 1 are bonded with a 21 µm pore size SPECTRA/MESH® polyester mesh material (Spectrum Labs, Ranch Dominguez, Calif., PN 148244) by the same procedure as described in Example 2. A 10 µL bed volume column is filled with PELLICULAR C18 (Alltech, Deerfield, Ill., PN 28551), particle size 30-50 µm. One end of the extraction column is connected to a pipettor pump (Gilson, Middleton, Wis., P-1000 PipetteMan) and the other end is movable and is connected to an apparatus where the materials may be taken up or deposited at different locations.

The extraction column consists of a 1 mL syringe (VWR, Brisbane, Calif., PN 53548-000), with one end connected to a pipettor pump (Gilson, Middleton, Wis., P-1000 PipetteMan) and the other end is movable and is connected to an apparatus where the materials may be taken up or deposited at different locations.

A 100 µL sample containing 0.01 µg of DNA is prepared using PCR amplification of a 110 bp sequence spanning the allelic MstII site in the human hemoglobin gene according to the procedure described in U.S. Pat. No. 4,683,195. A 10 µL concentrate of triethylammonium acetate (TEAA) is added so that the final volume of the solution is 110 µL and the concentration of the TEAA in the sample is 100 mM. The sample is introduced into the column and the DNA/TEAA ion pair complex is adsorbed.

The sample is blown out of the column and 10 µL of 50% (v/v) acetonitrile/water is passed through the column, desorbing the DNA, and the sample is deposited into a vial for analysis.

Example 7

Desalting Proteins with an Extraction Column

Columns from Example 1 are bonded with a 21 µm pore size SPECTRA/MESH® polyester mesh material (Spectrum Labs, Ranch Dominguez, Calif., PN 148244) by the same procedure as described in Example 2. A 10 µL bed volume column is filled with PELLICULAR C18 (Alltech, Deerfield, Ill., PN 28551), particle size 30-50 µm. One end of the extraction column is connected to a pipettor pump (Gilson, Middleton, Wis., P-1000 PipetteMan) and the other end is movable and is connected to an apparatus where the materials may be taken up or deposited at different locations.

The sample is a 100 µL solution containing 0.1 µg of Protein kinase A in a phosphate buffer saline (0.9% w/v NaCl, 10 mM sodium phosphate, pH 7.2) (PBS) buffer. Ten µL of 10% aqueous solution of trifluoroacetic acid (TFA) is added so that the final volume of the solution is 110 µL and the concentration of the TFA in the sample is 0.1%. The sample is introduced into the column and the protein/TFA complex is adsorbed to the reverse phase of the bed.

The sample is blown out of the column and 10 µL of 50% (v/v) acetonitrile/water is passed through the column, desorbing the protein from the bed of extraction media, and the sample is deposited into a vial for analysis.

Alternatively, the bed may be washed with 10 µL of aqueous 0.1% TFA. This solution is ejected from the column and the protein is desorbed and deposited into the vile.

If necessary, alternatively 1% heptafluorobutyric acid (HFBA) is used instead of TFA to reduce ion suppression effect when the sample is analyzed by electrospray ion trap mass spectrometry.

Example 8

Straight Connection Configuration

This example describes an embodiment wherein the column body is constructed by engaging upper tubular members and membrane screens in a straight configuration.

Figure 11:
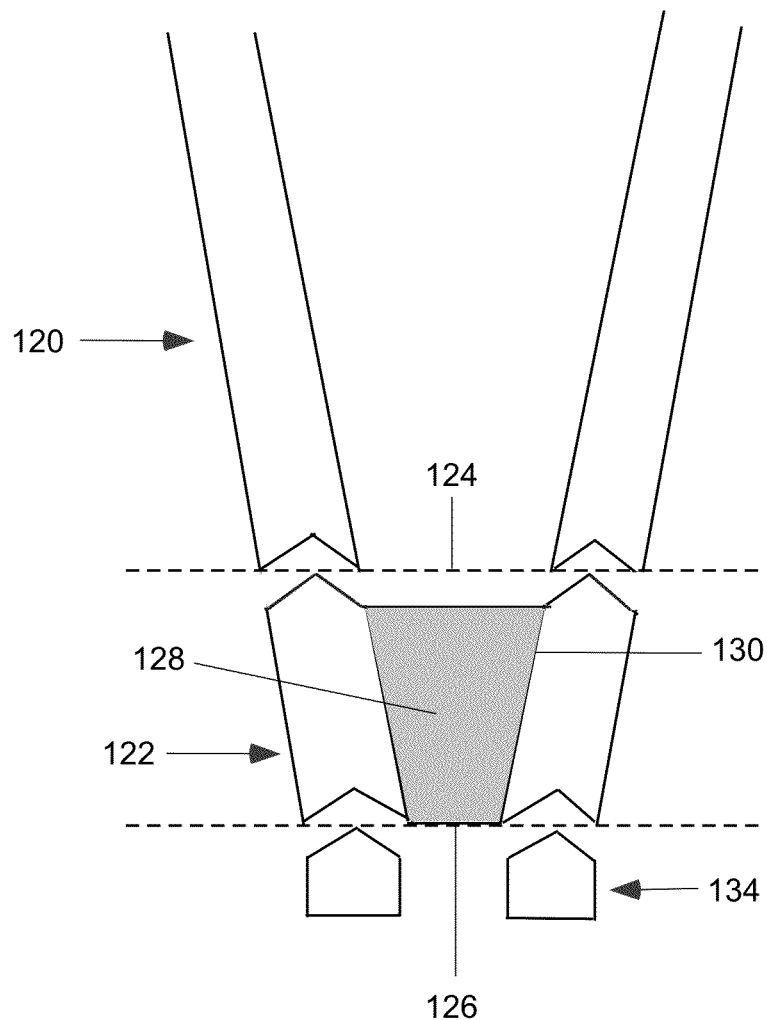
FIG. 11 depicts an embodiment of the invention with a straight connection configuration as described in Example 8.

Referring to FIG. 11, the column consists of an upper tubular member 120, a lower tubular member 122, a top membrane screen 124, a bottom membrane screen 126, and a lower tubular circle 134 to hold the bottom membrane screen in place. The top membrane screen is held in place by the upper and lower tubular members. The top membrane screen, bottom membrane screen and the channel surface 130 of the lower tubular member define an extraction media chamber 128, which contains a bed of extraction media 132 (i.e., packing material). The tubular members as depicted in FIG. 11 are frustoconical in shape, but in related embodiments could take other shapes, e.g, cylindrical.

To construct a column, various components are made by forming injected molded members from polypropylene or machined members from PEEK polymer to give specified column lengths and diameters and ends that can fit together, i.e., engage with one another. The configuration of the male and female portions of the column body is shaped differently depending on the method used to assemble the parts and the method used to keep the parts together.

The components are glued or welded. Alternatively, they are snapped together. In the case of snapping the pieces together, the female portion contains a lip and the male portion contains a ridge that will hold and seal the pieces once they are assembled. The membrane screen is either cut automatically during the assembly process or is trimmed after assembly.

Example 9

End Cap and Retainer Ring Configuration

Figure 12:
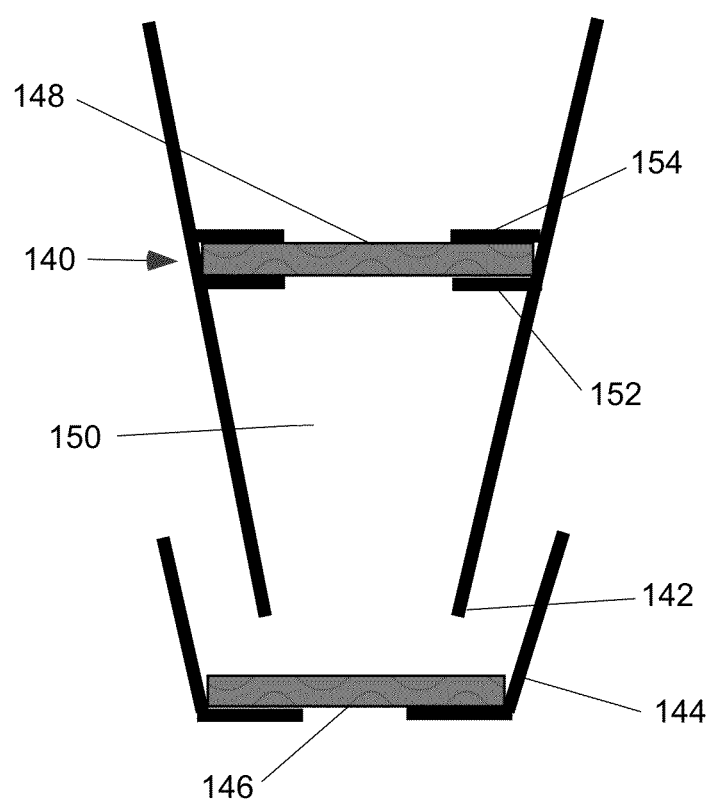
FIG. 12 depicts an embodiment of the invention with an end cap and retainer ring configuration as described in Example 9.

This example describes an embodiment where an end cap and retainer ring configuration is used to retain the membrane screens containing a 20 µl bed of column packing material. The embodiment is depicted in FIG. 12.

Referring to the figure, pipette tip 140 (VWR, Brisbane, Calif., PN 53508-987) was cut with a razor blade to have a flat and straight bottom end 142 with the smooth sides such that a press fit can be performed later. An end cap 144 was machined from PEEK polymer tubing to contain the bottom membrane screen 146.

Two different diameter screens were cut from polyester mesh (Spectrum Labs, Ranch Dominguez, Calif., PN 145836) by a circular cutting tool (Pace Punches, Inc., Irving, Calif.), one for the top membrane screen 148 and the other for the bottom membrane screen 146. The bottom membrane screen was placed into the end cap and pressed onto the end of the cut pipette tip.

A 20 µL volume bed of beads 150 was formed by pipetting a 40 µL of 50% slurry of protein G agarose resin into the column body.

Two retainer rings were used to hold the membrane screen in place on top of the bed of beads. The retainer rings were prepared by taking ⅛ inch diameter polypropylene tubing and cutting thin circles from the tubing with a razor blade. A first retainer ring 152 was placed into the column and pushed down to the top of the bed with a metal rod of similar diameter. The membrane screen 148 was placed on top of the first retainer ring and then a second retainer ring 154 was pushed down to "sandwich" the membrane screen while at the same time pushing the whole screen configuration to the top of the bed and ensuring that all dead volume was removed. The membrane is flexible and naturally forms itself to the top of the bed.

The column was connected to a 1000 μL pipettor (Gilson, Middleton, Wis., P-1000 PipetteMan) and water was pumped through the bed and dispensed from the bed. The column had low resistance to flow for water solvent.

While the invention has been described in connection with specific embodiments thereof, it will be understood that it is capable of further modifications and this application is intended to cover and variations, uses, or adaptations of the invention that follow, in general, the principles of the invention, including such departures from the present disclosure as come within known or customary practice within the art to which the invention pertains and as may be applied to the essential features hereinbefore set forth. Moreover, the fact that certain aspects of the invention are pointed out as preferred embodiments is not intended to in any way limit the invention to such preferred embodiments.

What is claimed is:

1. A low dead volume extraction column comprising:
   i) a column body having an open upper end for attachment to a pump, an open lower end for passing fluid into and out of the column body, and an open channel between the upper and lower end of the column body, wherein the column body comprises a pipette tip;
   ii) a bottom frit bonded to and extending across the open channel, the bottom frit having a pore volume;
   iii) a top frit bonded to and extending across the open channel between the bottom frit and the open upper end of the column body, the top frit having a pore volume, wherein the top frit or bottom frit are less than 350 microns thick, wherein the bottom frit is a membrane screen and the top frit is optionally a membrane screen and wherein the top frit or the bottom frit is comprised of nylon, polyester, polyamide, polycarbonate, cellulose, polyethylene, nitrocellulose, cellulose acetate, or polypropylene, and wherein the top frit, bottom frit, and channel surface define an extraction media chamber; and
   iv) a bed of extraction media positioned inside the extraction media chamber.

2. The low dead volume extraction column of claim 1, wherein the bottom frit is located at the open lower end of the column body.

3. The low dead volume extraction column of claim 1, wherein the bottom frit is less than 200 microns thick.

4. The low dead volume extraction column of claim 1, wherein the bottom frit has a pore volume equal to 10% or less of the interstitial volume of the bed of extraction media.

5. The low dead volume extraction column of claim 1, wherein the bottom frit has a pore volume of less than 1 microliter.

6. The low dead volume extraction column of claim 1, wherein the extraction media comprises a packed bed of gel-type packing material.

7. The low dead volume extraction column of claim 6, wherein the gel-type packing material is selected from the group consisting of agarose and sepharose.

8. The low dead volume extraction column of claim 1, wherein the bed of extraction media has a bed volume in the range of 0.5 to 20 microliters.

9. The low dead volume extraction column of claim 1, wherein the extraction media has an affinity for a biological molecule of interest.

10. The low dead volume extraction column of claim 9, wherein the affinity binding group is selected from the group consisting of Protein A, Protein G, Protein L and an immobilized metal.

11. The low dead volume extraction column of claim 1, wherein at the column body comprises a polycarbonate, polypropylene or polyethylene material.

12. The low dead volume extraction column of claim 1, wherein the top frit and the bottom frit are bonded to the column body by gluing or welding.

13. The low dead volume extraction column of claim 1, wherein the volume of the extraction media chamber at most 1000 microliters.

14. The low dead volume extraction column of claim 1, wherein the bed of extraction media has a dry weight of less than 10 mg.

15. The low dead volume extraction column of claim 1, wherein the extraction media comprises an extraction bead selected from the group consisting of affinity beads, ion exchange beads, hydrophobic interaction beads, reverse phase beads, agarose protein G beads, and Hypercell beads.

16. The low dead volume extraction column of claim 1, wherein the upper end of the column body is operatively attached to a pump for aspirating fluid through the lower end of the column body.

17. The low dead volume extraction column of claim 16, wherein the pump is a pipettor or a syringe.

18. The low dead volume extraction column of claim 1 comprising:
   i) a lower tubular member comprising the lower end of the column body, a first engaging end, and a lower open channel between the lower end of the column body and the first engaging end; and
   ii) an upper tubular member comprising the upper end of the column body, a second engaging end, and an upper open channel between the upper end of the column body and the second engaging end, the top membrane screen of the extraction column bonded to and extending across the upper open channel at the second engaging end;
   wherein the first engaging end engages the second engaging end to form a sealing engagement.

* * * * *

UNITED STATES PATENT AND TRADEMARK OFFICE
CERTIFICATE OF CORRECTION

| | |
|---|---|
| PATENT NO. | : 8,501,116 B2 |
| APPLICATION NO. | : 13/206435 |
| DATED | : August 6, 2013 |
| INVENTOR(S) | : Douglas T. Gjerde et al. |

It is certified that error appears in the above-identified patent and that said Letters Patent is hereby corrected as shown below:

In the Specification

Column 10, line 33 should read "glycoproteins from cells"

Signed and Sealed this
Seventeenth Day of May, 2016

Michelle K. Lee
*Director of the United States Patent and Trademark Office*